United States Patent [19]

Ueda et al.

[11] 4,443,443
[45] Apr. 17, 1984

[54] CEPHEM COMPOUNDS

[75] Inventors: Ikuo Ueda; Masaaki Matsuo, both of Toyonaka; Kiyoshi Tsuji, Osaka; Masayuki Kato, Mino, all of Japan

[73] Assignee: Fujisawa Pharmaceutical Co., Ltd., Osaka, Japan

[21] Appl. No.: 213,232

[22] Filed: Dec. 5, 1980

[30] Foreign Application Priority Data

Dec. 17, 1979 [JP] Japan .................. 54-7943363

[51] Int. Cl.³ .................. C07D 501/36; A61K 31/545
[52] U.S. Cl. ...................... 424/246; 544/21; 544/26; 544/27
[58] Field of Search .................. 544/27, 26, 21; 424/246

[56] References Cited

U.S. PATENT DOCUMENTS 4,278,793 7/1981 Dückheimer et al. .............. 544/21

FOREIGN PATENT DOCUMENTS 853545 10/1977 Belgium .
865632 10/1978 Belgium .

Primary Examiner—Nicholas S. Rizzo

Attorney, Agent, or Firm—Oblon, Fisher, Spivak, McClelland & Maier

[57] ABSTRACT

This invention relates to novel cephem compounds of high antimicrobial activity, of the formula:

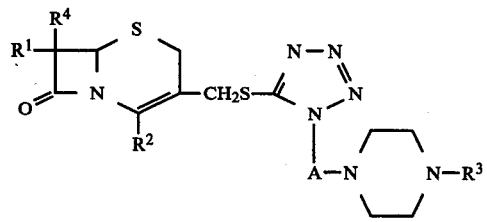

wherein
$R^1$ is amino or a protected amino group;
$R^2$ is carboxy or a protected carboxy group;
A is lower alkylene which may have an oxo group;
$R^3$ is carboxy, a protected carboxy group, lower alkyl, lower alkenyl, hydroxy (lower) alkyl, phenyl (lower) alkyl, phenyl, tolyl, xylyl, cumenyl, or naphthyl; and
$R^4$ is hydrogen or lower alkoxy, and pharmaceutically acceptable salts thereof.

20 Claims, No Drawings

CEPHEM COMPOUNDS

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

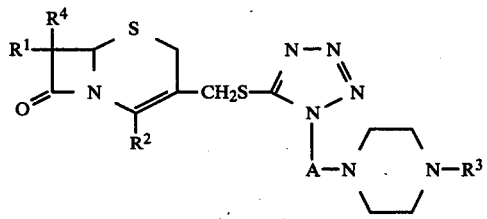

(I)

wherein
$R^1$ is amino or a substituted amino group;
$R^2$ is carboxy or a protected carboxy group;
A is lower alkylene which may have an oxo group;
$R^3$ is an organic group which may have suitable substituent(s); and
$R^4$ is hydrogen or lower alkoxy.

As to the object compounds (I) and the starting compounds of the present invention, it is to be understood that there may be one or more stereoisomeric pair(s) such as optical and/or geometrical isomers due to asymmetric carbon atom(s) and/or double bond(s), in the molecule, and these isomers are also included within the scope of the present invention.

The particulars of such isomers will be made more clear in the following explanation.

According to the present invention, the object compounds (I) can be prepared by the following processes which are illustrated in the following scheme.

Process 1

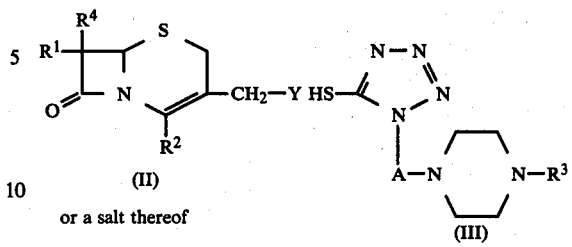

(II)
or a salt thereof or its reactive
derivative at
the mercapto
group or a salt
thereof

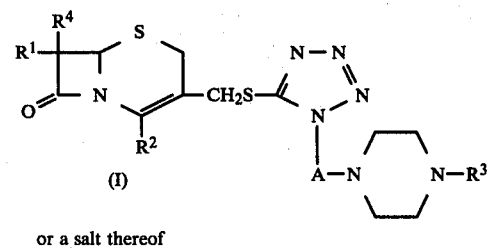

(I)
or a salt thereof

Process 2

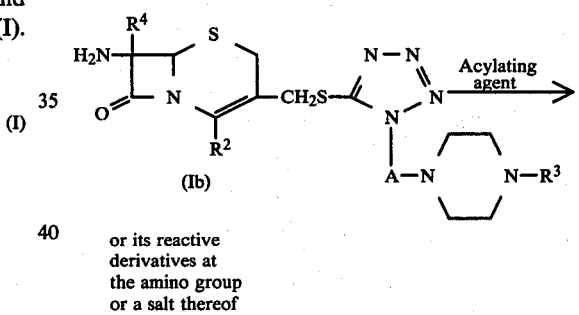

(Ib)
or its reactive
derivatives at
the amino group
or a salt thereof

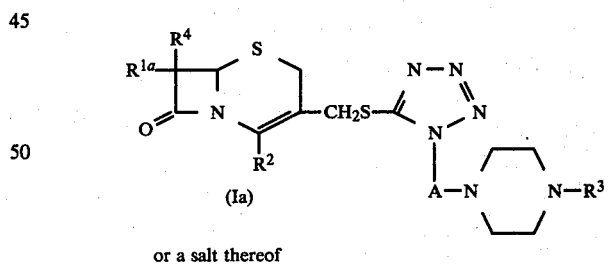

(Ia)
or a salt thereof

Process 3

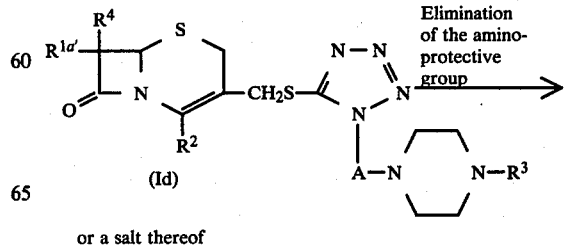

(Id)
or a salt thereof

-continued

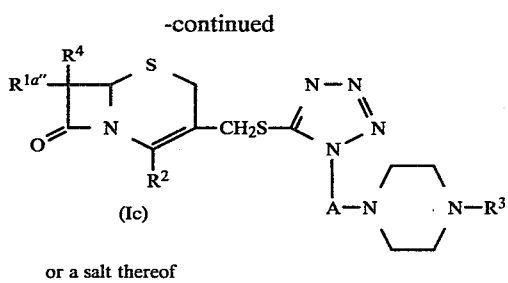

(Ic)

or a salt thereof wherein

R¹, R², R³, R⁴ and A are each as defined above;

Y is a group which can be substituted by a group of the formula:

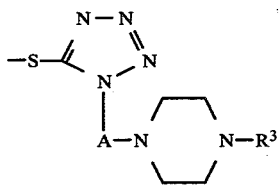

(wherein A and R³ are each as defined above)

R¹ᵃ is acylamino;

R¹ᵃ′ is acylamino having a protected amino group;

R¹ᵃ″ is acylamino having an amino group.

Among the starting compounds of the present invention the compounds (III) and some of the compounds (II) are novel and can be prepared by the processes which are illustrated in the following schemes.

Process A

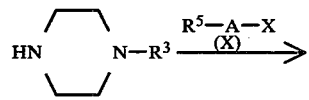

(XI)
or a salt thereof

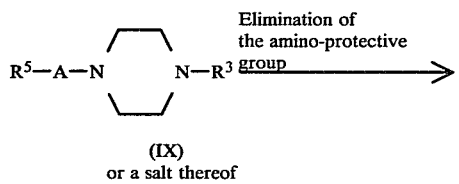

(IX)
or a salt thereof

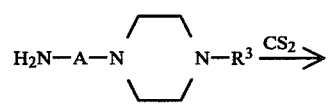

(VIII)
or a salt thereof

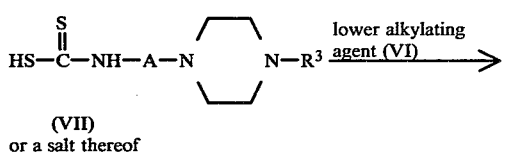

(VII)
or a salt thereof

-continued

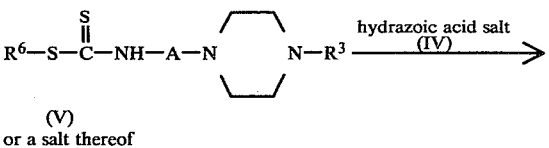

(V)
or a salt thereof

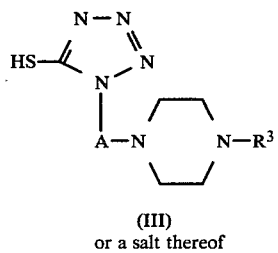

(III)
or a salt thereof

Process B

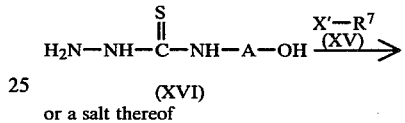

(XVI)
or a salt thereof

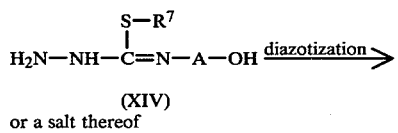

(XIV)
or a salt thereof

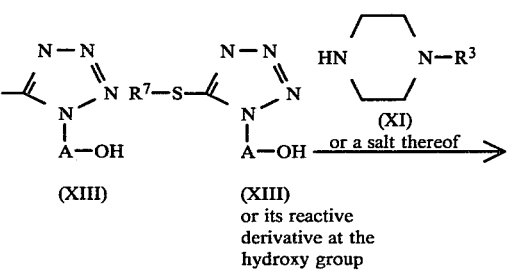

(XIII)   (XIII)
          or its reactive
          derivative at the
          hydroxy group

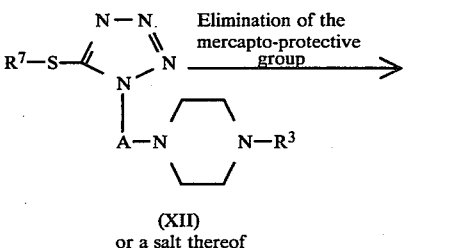

(XII)
or a salt thereof

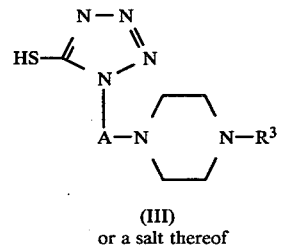

(III)
or a salt thereof

Process C

-continued

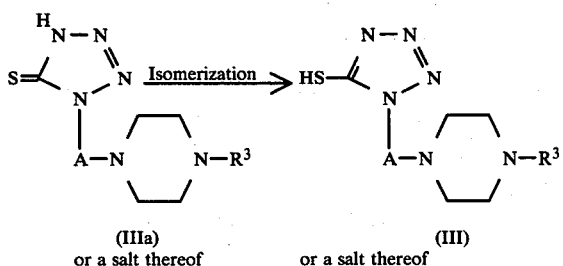

(IIIa) or a salt thereof    (III) or a salt thereof

Process D

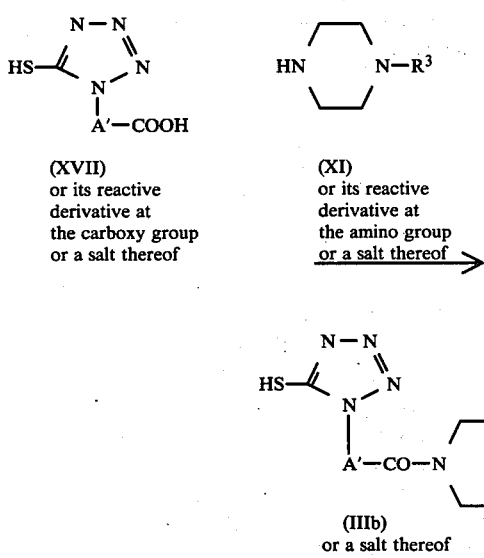

Process E

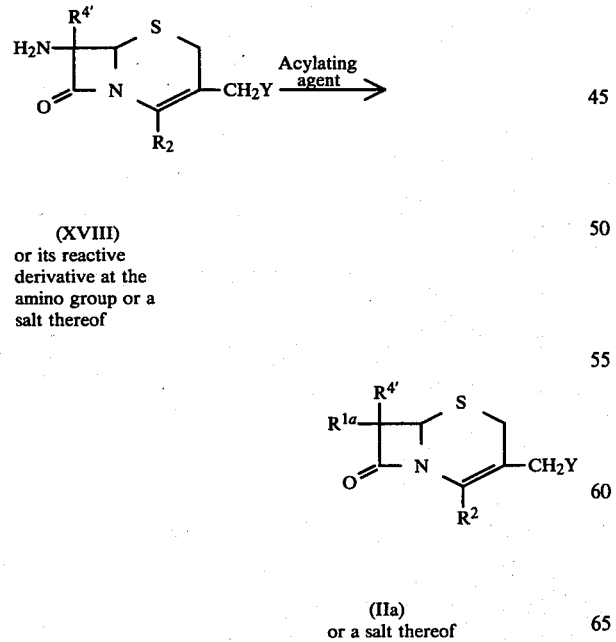

Process F

-continued

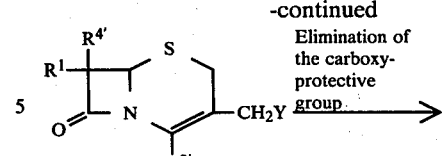

(IIc) or a salt thereof

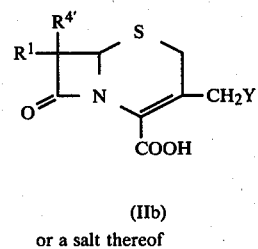

(IIb) or a salt thereof wherein
$R^1$, $R^{1a}$, $R^2$, $R^3$, A and Y are each as defined above;
$R^{2'}$ is a protected carboxy group;
$R^{4'}$ is lower alkoxy;
$R^5$ is a protected amino group;
$R^6$ is lower alkyl;
$R^7$ is a mercapto-protective group;
A' is lower alkylene; and
X and X' are each an acid residue.

Concerning the starting thiol compounds (III), (IIIb) and (XVII), there are tautomeric isomers as shown by the following equilibrium:

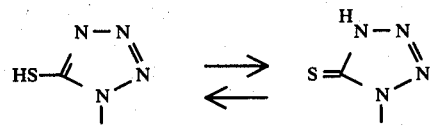

These types of tautomerism between 1-substituted 1H-tetrazole-5-thiol compounds and 1-substituted 4,5-dihydro-1H-tetrazole-5-thione compounds as stated above have been well known in the arts, and it is obvious to a person skilled in the arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, starting compounds including the group of such tautomeric isomers are represented by using one of the expressions therefor, i.e. 1-substituted 1H-tetrazole-5-thiol and the formula:

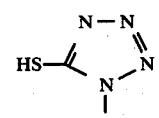

only for the convenient sake.

Suitable pharmaceutically acceptable salts of the object compounds (I) are conventional non-toxic salts and may include a metal salt such as an alkali metal salt (e.g.

sodium salt, potassium salt, etc.) and an alkaline earth metal salt (e.g. calcium salt, magnesium salt, etc.), ammonium salt, an organic amine salt (e.g. trimethylamine salt, triethylamine salt, pyridine salt, picoline salt, dicyclohexylamine salt, N,N'-dibenzylethylenediamine salt, etc.), an organic acid salt (e.g. formate, trifluoroacetate, maleate, tartrate, methanesulfonate, benzenesulfonate, toluenesulfonate etc.), an inorganc acid salt (e.g. hydrochloride, hydrobromide, sulfate, phosphate, etc.), or a salt with an amino acid (e.g. arginine, aspartic acid, lysine, glutamic acid, etc.), and the like.

In the above and subsequent description of the present specification, suitable examples and illustrations for the various definitions to be included within the scope of the present invention are explained in details as follows.

The term "lower" is intended to mean 1 to 6 carbon atoms and the term "higher" is intended to mean 7 to 18 carbon atoms, unless otherwise indicated.

Suitable "substituted amino group" may include an amino group substituted by a conventional substituent used in Cephalosporin and Penicillin compounds such as acyl as mentioned below, ar(lower)alkyl (e.g. benzyl, phenethyl, trityl, etc.) or the like.

Suitable "acyl" and "acyl moiety" in the terms "acylamino", "acylamino having a protected amino group", "acylamino having an amino group" and "acyloxy" may include carbamoyl, an aliphatic acyl group, an acyl group containing an aromatic ring (hereinafter referred to as aromatic acyl) and an acyl group containing a heterocyclic ring (hereinafter referred to as heterocyclic acyl).

Suitable example of said acyl may be illustrated as follows:

Aliphatic acyl such as lower or higher alkanoyl (e.g. formyl, acetyl, succinyl, hexanoyl, heptanoyl, stearoyl, etc.);
lower or higher alkoxycarbonyl (e.g. methoxycarbonyl, ethoxycarbonyl, tert-butoxycarbonyl, tert-pentyloxycarbonyl, heptyloxycarbonyl, etc.);
lower or higher alkanesulfonyl (e.g. methanesulfonyl. ethanesulfonyl, etc.); or the like;
Aromatic acyl such as aroyl (e.g. benzoyl, toluoyl, naphthoyl, phthaloyl etc.);
ar(lower)alkanoyl (e.g. phenylacetyl, phenylpropionyl, etc.);
aryloxycarbonyl (e.g. phenoxycarbonyl, naphthyloxycarbonyl, etc.);
ar(lower)alkoxycarbonyl (e.g. benzyloxycarbonyl, phenethyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonly, etc.); or the like;
Heterocyclic acyl such as
heterocycliccarbonyl (e.g. theonoyl, furoyl, nicotinoyl, etc.);
heterocyclic(lower)alkanoyl (e.g. thienylacetyl, thiazolylacetyl, dithiinylacetyl, pyridylacetyl, pyrimidinylacetyl, triazolylacetyl, tetrazolylacetyl, furylacetyl, oxazolylacetyl, thiazolylpropionyl, etc.);
heterocyclicglyoxyloyl (e.g. thiazolylglyoxyloyl, thienylglyoxyloyl, etc.); or the like.

The acyl and acyl moiety as stated above may have one or more, same or different, suitable substituent(s) such as lower alkyl (e.g. methyl, ethyl, propyl, etc.); lower alkoxy (e.g. methoxy, ethoxy, propoxy etc.); lower alkylthio (e.g. methylthio, ethylthio, etc.); lower alkylamino (e.g. methylamino, etc.); halogen (e.g. chlorine, bromine, fluorine or iodine); carboxy protected carboxy group as mentioned below; amino; protected amino group as mentioned below; hydroxy; protected hydroxy such as tetrahydropyranyloxy or acyloxy wherein the acyl moiety is as stated above; imino; oxo; a group of the formula: $=N-OR^8$ wherein $R^8$ is hydrogen, lower alkyl (e.g. methyl, ethyl, propyl, isopropyl, butyl, pentyl hexyl, etc.) or ($C_3$ to $C_8$) cycloalkenyl (e.g. cyclopropenyl, cyclobutenyl, cyclopentenyl, cyclohexenyl, etc.); or the like.

In this connection, when the acyl and acyl moiety have a group of the formula: $=N-OR^8$ (wherein $R^8$ is as defined above) as substituent(s), there are geometrical isomers (syn and anti isomers) due to the presence of double bond. And, for example, the syn isomer means one geometrical isomer having the group of the formula:

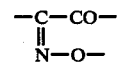

and the corresponding anti isomer means the other geometrical isomer having the group of the formula:

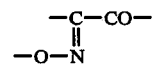

Suitable "protected carboxy group" may include an esterified carboxy and the like, and suitable examples of the ester moiety in said esterified carboxy may be the ones such as lower alkyl ester (e.g. methyl ester, ethyl ester, propyl ester, isopropyl ester, butyl ester, isobutyl ester, pentyl ester, hexyl ester, 1-cyclopropylethyl ester, etc.) which may have at least one suitable substituent(s), for example, lower alkanoyloxy(lower) alkyl ester (e.g. acetoxymethyl ester, propionyloxymethyl ester, butyroyloxymethyl ester, valeryloxymethyl ester, pivaloyloxymethyl ester, 2-acetoxyethyl ester, 2-propionyloxyethyl ester, hexanoyloxymethyl ester, etc.), lower alkanesulfonyl(lower)alkyl ester (e.g. 2-mesylethyl ester, etc.) or mono (or di or tri)-halo(lower-)alkyl ester (e.g. 2-iodoethyl ester, 2,2,2-trichloroethyl ester, etc.); lower alkenyl ester (e.g. vinyl ester, allyl ester, etc.);
lower alkynyl ester (e.g. ethynyl ester, propynyl ester, etc.);
ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis-(methoxyphenyl)methyl ester, 3,4-dimethoxybenzyl ester, 4-hydroxy-3,5-ditertiarybutylbenzyl ester, etc.); aryl ester which may have at least one suitable substituent(s) (e.g. phenyl ester, 4-chlorophenyl ester, tolyl ester, tertiarybutylphenyl ester, xylyl ester, mesityl ester, cumenyl ester, etc.), and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, 1-cyclopropylethoxycarbonyl, etc.) and mono(or di or tri)-phenyl(- lower)-alkoxycarbonyl (e.g. benzyloxycarbonyl, benzhydryloxycarbonyl, etc.).

Suitable "lower alkylene" and "lower alkylene moidety" in the term "lower alkylene which may have an oxo group" may include straight or branched one and may include methylene, ethylene, trimethylene, propylene, tetramethylene, pentamethylene, hexamethylene and the like.

Suitable "organic group which may have suitable substituent(s)" may include carboxy, protected carboxy group as stated above, an aliphatic and aromatic group, for example, lower alkyl (e.g. methyl, ethyl, propyl, isopropyl, butyl, isobutyl, tert-butyl, pentyl, neopentyl, tert-pentyl, hexyl, etc.);

lower alkenyl (e.g. vinyl, 1-propenyl, allyl, 1-methylallyl, 1 or 2 or 3-butenyl, 1 or 2 or b 3 or 4-pentenyl, 1 or 2 or 3 or 4 or 5-hexenyl, etc.);

aryl (e.g. phenyl, tolyl, xylyl, cumenyl, naphthyl, etc.);

ar(lower)alkyl such as phenyl(lower)alkyl (e.g. benzyl, phenethyl, phenylpropyl, etc.);

hydroxy(lower)alkyl (e.g., hydroxymethyl, hydroxyethyl, hydroxypropyl, hydroxybutyl, etc.); and the like.

Suitable "lower alkoxy" may include methoxy, ethoxy, propoxy, isopropoxy, butoxy and the like.

Suitable "lower alkyl" means straight or branched one and may include methyl, ethyl, propyl, isopropyl, butyl, isobutyl, tert-butyl, pentyl, hexyl and the like.

Suitable example of Y may include an acid residue (e.g., azido, halogen as mentioned above, acyloxy as mentioned above, etc.) and the like.

Suitable "protected amino group" and "protected amino moiety" in the term "acylamino having a protected amino group" may include an acylamino, wherein an acyl moiety is as mentioned above, and an amino group substituted by a conventional protecting group such as ar(lower)-alkyl (e.g., benzyl, trityl, etc.) and the like.

Suitable "acid residue" for X and X' may include halogen (e.g. chlorine, bromine, iodine etc), azido, and the like.

Suitable "mercapto-protective group" may include a conventional protective group such as lower alkyl as mentioned above, ar(lower)alkyl, for example, phenyl (lower)alkyl (e.g., benzyl, phenethyl, phenylpropyl, etc.) and the like.

The processes for preparing the object compounds of the present invention are explained in detail in the following.

Process 1

The object compound (I) or a salt thereof can be prepared by reacting the compound (II) or a salt thereof with the compound (III) or its reactive derivative at the mercapto group or a salt thereof.

Suitable salts of the compound (II) and (III) are each referred to the ones exemplified for the compound (I).

Suitable reactive derivative at the mercapto group in the compound (III) may include a metal salt such as an alkali metal salt (e.g. sodium salt, potassium salt, etc.), an alkaline earth metal salt (e.g., magnesium salt, etc.) or the like.

The reaction is usually carried out in a solvent such as water, acetone, chloroform, nitrobenzene, methylene chloride, ethylene chloride, dimethylformamide, methanol, ethanol, ether, tetrahydrofuran or any other conventional solvents which do not adversely influence the reaction, preferably in ones having strong polarity, which may be used as a mixture with water.

When the compound (II) and/or the compound (III) are used in free form in the reactions, the reaction is preferably carried out in the presence of a base such as alkali metal hydroxide, alkali metal carbonate, alkali metal bicarbonate, trialkylamine, pyridine, or a Lewis acid such as boron trifluoride or the like, and preferably carried out around neutral conditions. The reaction temperature is not critical and the reaction is usually carried out at ambient temperature or under warming.

The present invention includes, within its scope, the cases that a protected amino and/or a protected carboxy group are converted into the corresponding free amino and/or the free carboxy group during the reaction or the post-treating step of the present process.

Process 2

The object compound (Ia) or a salt thereof can be prepared by reacting the compound (Ib) or its reactive derivatives at the amino group or a salt thereof with an acylating agent.

Suitable reactive derivatives at the amino group of the compound (Ib) may include conventional ones such as Schiff's base type imino or its tautomeric enamine type derivatives formed by the reaction of the compound (Ib) with a carbonyl compound (e.g. aldehyde, ketone, etc.), isocyanate;

silyl derivatives formed by the reaction of the compound (Ib) with a silyl comound [e.g. bis(trimethylsilyl)acetamide, trimethylsilylacetamide, etc.];

derivatives formed by the reaction of the compound (Ib) with phosphorus trichloride or phosgene, or the like.

Suitable salts of the compound (Ib) can be referred to the ones as exemplified for the compound (I).

The acylating agent to be used for the present reaction may include one of the formula:

$$R^9-OH \quad (XIX)$$

wherein $R^9$ is acyl, or its reactive derivatives or a salt thereof.

Suitable acyl can be referred to those exemplified hereinbefore.

Suitable reactive derivatives of the compound (XIX) may include an acid halide, an acid anhydride, an activated amide, an activated ester, and the like.

The suitable example may be an acid chloride; an acid azide;

a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.);

a symmetrical acid anhydride;

an activated amide with imidazole, 4-substituted imidazole, dimethylpyrazole, triazole or tetrazole; an activated ester [e.g. cyanomethyl ester, methoxymethyl ester, dimethyliminomethyl  ester, vinyl ester, propargyl ester, p-nitrophenyl ester, 2,4-dinitrophenyl ester, trichlorophenyl ester, pentachlorophenyl ester, mesyl-phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole, and the like.]

These reactive derivatives can optionally be selected from them according to the kind of the compound (XIX) to be used.

The salts of the compound (XIX) may be salt with an inorganic base such as an alkali metal salts (e.g. sodium or potassium salt) or an alkaline earth metal salt (e.g. calcium or magnesium salt), a salt with an organic base such as trimethylamine, triethylamine, dicyclohexylamine or the like.

The present reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. Among these solvents, hydrophilic solvents may be used in a mixture with water.

When the acylating agent is used in a free acid form or its salt form in the reaction, the reaction is preferably carried out in the presence of a conventional condensing agent such as carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonylbis(2-mesylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vilsmeier reagent [e.g. (chloromethylene)dimethylammonium chloride, a compound formed by the reaction of dimethylformamide with phosphorus oxychloride, etc.] or the like.

The reaction may also be carried out in the presence of an inorganic or an organic base such as an alkali metal bicarbonate, alkali metal carbonate, tri(lower)alkylamine, pyridine, di(lower)alkylpyridine, N-(lower)alkylmorphorine, N,N-di(lower)alkylbenzylamine, N,N-di(lower)alkylaniline, or the like. When the base or the condensing agent is in liquid, it can be used also as a solvent. The reaction temperature is not critical, and the reaction is usually carried out under cooling or at ambient temperature.

Process 3

The object compound (Ic) or a salt thereof can be prepared by subjecting the compound (Id) or a salt thereof to the elimination reaction of the amino-protective group.

Suitable salts of the compound (Id) may include a metal salt, ammonium salt, an organic amine salt and the like as aforementioned.

The present elimination reaction is carried out in accordance with a conventional method such as hydrolysis; reduction; elimination using a Lewis acid; a method by reacting the compound (Id), wherein the protective group is an acyl group, with an iminohalogenating agent and then with an imino-etherifying agent, and, if necessary, subjecting the resulting compound to hydrolysis; or the like.

The hydrolysis may include a method using an acid or base or hydrazine and the like. These methods may be selected depending on the kind of the protective groups to be eliminated.

Among these methods, hydrolysis using an acid is one of the common and preferable methods for elimination of an acyl group.

Suitable acid may include an organic or an inorganic acid, for example, formic acid, trifluoroacetic acid, benzenesulfonic acid, p-toluenesulfonic acid, hydrochloric acid and the like, and preferable acids are those which can easily be removed from the reaction mixture by a conventional manner such as distillation under reduced pressure, for example, formic acid, trifluoroacetic acid, hydrochloric acid, etc. The acid suitable for the reaction can be selected according to the kind of protective groups to be eliminated. When the elimination reaction is conducted with an acid, it can be carried out in the presence or absence of a solvent. Suitable solvents may include an organic solvent, water or a mixed solvent thereof. When trifluoroacetic acid is used, the elimination reaction may preferably be carried out in the presence of anisole.

The hydrolysis using hydrazine is commonly applied for eliminating the protective groups, for example, succinyl or phthaloyl.

The hydrolysis using a base is preferably applied for elimination of an acyl group. Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,2]octane, 1,5-diazabicyclo[5,4,0]undecene-5 or the like. The hydrolysis using a base is often carried out in water or a hydrophilic organic solvent or a mixed solvent thereof.

Among the protective group, the acyl group can generally be eliminated by hydrolysis as mentioned above or by the other conventional hydrolysis. In case that the acyl group is halo(lower)alkoxycarbonyl or 8-quinolyloxycarbonyl, they are eliminated by treating with a heavy metal such as copper, zinc or the like.

The reductive elimination is generally applied for eliminating the protective group, for example, halo(lower or higher)alkoxycarbonyl (e.g. trichloroethoxycarbonyl, etc.), substituted or unsubstituted ar(lower)alkoxycarbonyl (e.g. benzyloxycarbonyl, etc.), etc. Suitable reduction may include, for example, reduction with an alkali metal borohydride (e.g. sodium borohydride, etc.), reduction using a combination of a metal (e.g. zinc, zinc amalgam, etc.) and an organic or inorganic acid (e.g. acetic acid, propionic acid, hydrochloric acid, etc.), catalytic reduction, and the like.

Suitable iminohalogenating agents used in a method as mentioned above may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out at ambient temperature or under cooling. Suitable iminoetherifying agents reacted with thus obtained reaction product may include an alcohol, metal alkoxide and the like. Suitable alcohol may include alkanol (e.g. methanol, ethanol, propanol, isopropanol, butanol, tert-butanol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like.

The reaction temperature is not critical, and the reaction is usually carried out under cooling at ambient temperature or under warming.

The processes for preparing the starting compounds (III) and (II) are explained in detail as follows.

Suitable salts of the compounds (IIa)-(IIc), (IIIa)-(IIIb), (V), (VII)-(IX), (XI)-(XII), (XIV) and (XVI)-(XIX) may include the ones as exemplified for the compound (I).

Process A (1) (XI)+(X)→(IX)

The compound (IX) or a salt thereof can be prepared by reacting the compound (XI) or a salt thereof with the compound (X).

The present reaction may be carried out in the presence of an organic or inorganic base such as alkali metal bicarbonate, alkali metal carbonate, alkaline earth metal bicarbonate, alkaline earth metal carbonate, alkali metal hydroxide, alkaline earth metal hydroxide, tri(lower)alkylamine, N,N-di(lower)alkyl arylamine, pyridine or the like.

The present reaction is usually carried out in a solvent such as acetone, N,N-dimethylformamide or any other solvents which do not adversely affect the reaction.

The reaction temperature is not critical and the reaction is preferably carried out from at ambient temperature to under heating.

(2) (IX)→(VII)

The compound (VIII) or a salt thereof can be prepared by subjecting the compound (IX) or a salt thereof to the elimination of the amino-protective group.

This elimination reaction can be carried out in a similar manner to that of aforementioned Process 3.

(3) (VIII)→(VII)

The compound (VII) or a salt thereof can be prepared by reacting the compound (VIII) or a salt thereof with carbon disulfide.

The present reaction is usually carried out in a solvent such as alcohol (e.g., methanol, etc.) or any other solvents which do not adversely affect the reaction.

The reaction temperature is not critical and the reaction is preferably carried out under cooling to warming.

(4) (VII)+(VI)→(V)

The compound (V) or a salt thereof can be prepared by reacting the compound (VII) or a salt thereof with a lower alkylating agent (VI).

Suitable "lower alkylating agent" may include lower alkyl halide (e.g. methyl iodide, methyl chloride, methyl bromide, ethyl iodide, etc.) and the like.

The present reaction is preferably carried out in a solvent such as alcohol (e.g. ethanol, etc.) or any other solvents which do not adversely affect the reaction.

The reaction temperature is not critical and the reaction is preferably carried out under cooling to warming.

(5) (V)+(IV)→(III)

The compound (III) or a salt thereof can be prepared by reacting the compound (V) or a salt thereof with a hydrazoic acid salt (IV).

Suitable "hydrazoic acid salt" may include an alkali metal azido (e.g. sodium azido, potassium azido, etc.) and the like.

The present reaction is usually carried out in a solvent such as water, alcohol (e.g., methanol, ethanol, etc.) or a mixed solvent thereof or any other solvents which do not adversely affect the reaction.

The reaction temperature is not critical and the reaction is preferably carried out from at ambient to under heating.

Process B (1) (XVI)+(XV)→(XIV)

The compound (XIV) or a salt thereof can be prepared by reacting the compound (XVI) or a salt thereof with the compound (XV).

The present reaction is usually carried out in a solvent such as water, alcohol (e.g., methanol, ethanol, etc.) or a mixed solvent thereof, or any other solvents which do not adversely affect the reaction.

The reaction temperature is not cirtical and the reaction is preferably carried out under cooling to warming.

(2) (XIV)→(XIII)

The compound (XIII) can be prepared by subjecting the compound (XIV) or a salt thereof to the diazotization reaction.

The present diazotization can be carried out by using a conventional diazotizing agent such as nitrous acid, [which may be prepared in situ by reaction of an alkali metal nitrite with an acid (e.g. hydrochloric acid, etc.)], nitrosyl-chloride, lower alkyl nitrite (e.g., t-butyl nitrite, etc.) or the like.

The present reaction may be carried out in the presence of an organic or inorganic acid such as hydrochloric acid, acetic acid or the like.

The present reaction may be carried out in a solvent such as alcohol (e.g., methanol, ethanol, etc.) or any other solvents which do not adversely affect the reaction.

The reaction temperature is not critical and the reaction is preferably carried out under cooling or at ambient temperature.

(3) (XIII)+(XI)→(XII)

The compound (XII) or a salt thereof can be prepared by reacting the compound (XIII) or its reactive derivative at the hydroxy group with the compound (XI) or a salt thereof.

Suitable reactive derivative at the hydroxy group of the compoound (XIII) may include the compound (XIII) wherein the hydroxy group is transformed into an acid residue such as halogen (e.g., chlorine, bromine, etc.), arenesulfonyloxy (e.g., p-toluenesulfonyloxy, p-nitrobenzenesulfonyl, etc.), haloformyloxy (e.g., chloroformyloxy, etc.) or the like.

The present reaction can be carried out in a similar manner to that of aforementioned Process A-1).

(4) (XII)→(III)

The compound (III) or a salt thereof can be prepared by subjecting the compound (XII) or a salt thereof to the elimination reaction of the mercapto-protective group.

The present elimination reaction may be carried out in accordance with a conventional method such as hydrolysis using an organic or inorganic acid (e.g. acetic acid, hydrobromic acid, etc.) or the like.

The present reaction is usually carried out in a solvent such as water or any other solvents which do not adversely affect the reaction.

The reaction temperature is not cirtical and the reaction is preferably carried out under cooling to heating.

Process C (IIIa)→(III)

The compound (III) or a salt thereof can be prepared by isomerizing the compound (IIIa) or a salt thereof.

The present isomerization may be carried out in the presence of an organic or inorganic acid (e.g., hydrochloric acid, acetic acid, etc.).

The present reaction is usually carried out in a solvent such as water or any other solvents which do not adversely affect the reaction.

The reaction temperature is not cirtical and the reaction is preferably carried out under cooling to warming.

Process D (XVII)+(XI)→(IIIb)

The compound (IIIb) or a salt thereof can be prepared by reacting the compound (XVII) or its reactive derivative at the carboxy group or a salt thereof with the compound (XI) or its reactive derivative at the amino group or a salt thereof.

The present reaction can be carried out in a similar manner to that of aforementioned Process 2.

Process E (XVIII)→(IIa)

The compound (IIa) or a salt thereof can be prepared by reacting the compound (XVIII) or its reactive derinative at the amino group or a salt thereof with an acylating agent.

The present reaction can be carried out in a similar manner to that of aforementioned Process 2.

Process F (IIc)→(IIb)

The compound (IIb) or a salt thereof can be prepared by subjecting the compound (IIc) or a salt thereof to the elimination reaction of the carboxy-protective group.

The present elimination reaction is carried out in accordance with a connectional method such as hydrolysis, elimination using Lewis acid [preferably in the presence of cation trapping agents (e.g., anisole, etc.)], reduction or the like.

The present reaction is usually carried out in a solvent such as nitroalkane (e.g., nitromethane, etc.), alkylene halide (e.g., methylene chloride, etc.) or any other solvents which do not adversely affect the reaction.

The reaction temperature is not cirticul and the reaction is preferably carried out under cooling to warming.

The present invention includes, within its scope, the cases that protected amino and/or protected carboxy and/or protected hydroxy group(s) are transformed into the corresponding free amino and/or carboxy and/or hydroxy group(s) according to the reaction conditions and kinds of the protective groups in the course of the aforementioned reactions and/or in post-treatment of the reactions in Processes 1 to 3 and A to F.

In the aforementioned reactions and/or the post-treating of the reactions in Processes 1 to 3 and A to F of the present invention, the aforementioned geometrical isomer and/or tautomeric isomer may be occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now, in order to show the utility of the object compounds (I), test data on anti-microbial activity of a representative compound of the present invention are shown below.

Test method

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu g/ml$ after incubation at 37° C. for 20 hours.

Test compound (1) 7-[2-methoxyimino-2-(2-aminothiazol-4-yl)acetamido]-3-[1-[3-(4-methyl-1-piperazinyl)-propyl]-1H-tetrazol-5-yl]thiomethyl-3-cephem-4-carboxylic acid (syn isomer).

(2) 7-[2-methoxyimino-2-(2-aminothiazol-4-yl)acetamido]-3-[1-[2-(4-methyl-1-piperazinyl)ethyl]-1H-tetrazol-5-yl]thiomethyl-3-cephem-4-carboxylic acid (syn isomer).

(3) 7-[2-methoxyimino-2-(2-aminothiazol-4-yl)acetamido]-3-[1-(4-methyl-1-piperazinyl)carbonylmethyl-1H-tetrazol-5-yl]thiomethyl-3-cephem-4-carboxylic acid (syn isomer).

| Test Microorganism | Test result M.I.C. (μg/ml) | | |
|---|---|---|---|
| | Compound (1) | Compound (2) | Compound (3) |
| Escherichia coli 31 | 0.05 | 0.05 | 0.10 |
| Klebsiella pneumoniae 20 | 0.10 | 0.10 | 0.10 |
| Proteus vulgaris 2 | 0.39 | 0.39 | 0.10 |

The following preparations and examples are given for the purpose of illustrating the present invention.

Preparation 1

(1) To the solution of N-(3-bromopropyl)phthalimide (402 g) in acetone (2.5 l) were added 1-methylpiperazine (225 g) and potassium carbonate (415 g). The resulting mixture was refluxed with stirring for 3.5 hours. The reaction mixture was cooled and then filtered. The filter cake was washed with acetone (500 ml). The filtrate and washing were combined and evaporated under reduced pressure. The remaining starting materials in the residnal oil were azeotropically removed with benzene to give an oil of N-[3-(4-methyl-1-piperazinyl)propyl]phthalimide (502 g). I.R. (Film): 1770,1700 cm$^-$.

(2) To a solution of N-[3-(4-methyl-1-piperazinyl)propyl]phthalimide (502 g) in ethanol (3.0 l) was added 100% hydrazine hydrate (187.6 g). The nesulting mixture was refluxed with stiving for 1.5 hours. The reaction mixture was cooled and then filtered. The filter cake was washed with ethanol (1 l). The filtrate and washing were combined and evaporated, under reduced pressure. The residual oil was distilled under reduced pressure to give 3-(4-methyl-1-piperazinyl)propylamine (146.6 g), bp 34 mmHg/127° to 128° C.

(3) To a solution of potassium hydroxide (57.3 g) in methanol (250 ml) was added 3-(4-methyl-1-piperazinyl)propylamine (146 g) and thereto was added carbon disulfide (70.6 g) with stirring under ice cooling over a period of 40 minutes. The resulting mixture was stirred for 3.5 hours under ice cooling. The reaction mixture was evaporated under reduced pressure. The residual oil was dissolved in water (400 ml) and washed with diethyl ether twice. The washed aqueous layer was ice-cooled and thereto was added methyl iodide (132.1 g) with stirring. The resulting mixture was stirred for 2 hours under ice-cooling, and extracted with ethyl acetate (400 ml×3) and chloroform (400 ml×2). The extracts were combined, dried over magnesium sulfate and then evaporated under reduced pressure to give methyl N-[3-(4-methyl-1-peperazinyl)propyl]dithiocarbamate (139.3 g).

Thus obtained product was used directly in the next step reaction without further purification.

(4) To a solution of methyl N-[3-(4-methyl-1-piperazinyl)propyl]dithiocarbamate obtained in Preparation 1 (3) (139.3 g) in a mixture of water (420 ml) and ethanol (280 ml) was added sodium azide (47.6 g). The resulting mixture was refluxed with stirring for 3 hours. The reaction mixture was concentrated under reduced prossure. The concentrate was washed successively with ethyl acetate and diethyl ether and then evaporated. To the residue was added ethanol and the mixture was filtered. The filtrate was evaporated under reduced pressure, and to the residual oil was added 6 N hydrochloric acid. The mixture was evaporated under reduced pressure. The residue was recrystallized from isopropyl alcohol containing water to give 1-[3-(4-methyl-1-piperazinyl)propyl]-1H-tetrazole-5-thiol dihydrochloride (48.1 g), mp 239° to 243° C.

N.M.R. (D$_2$O, δ): 2.3–2.8 (2H, m), 3.07 (3H, s) 3.3–3.7 (2H, m), 3.75 (8H, s), 4.42 (2H, t, J=6 Hz).

Preparation 2

(1) To the solution of N-(3-bromopropyl)phthalimide (20.1 g) in acetone (225 ml) were added.

1-benzyl piperazine (19.8 g) and potassium carbonate (31.1 g). The resulting mixture was refluxed with stirring for 3 hours. The reaction mixture was cooled and then filtered. The filter cake was washed with acetone. The filtrate and washing were combined and evaporated under reduced pressure to give the oily crude product of the object compound (36.2 g). This oily product was subjected to column chromatography on silica gel. The fractions containing the object compound were collected to give an oil of N-[3-(4-benzyl-1-piperazinyl)propyl]phthalimide (22.4 g).

(2) To a solution of N-[3-(4-benzyl-1-piperazinyl)propyl]phthalimide (22.4 g) in ethanol (250 m) was added 100% hydrazine hydrate (8.02 g). The resulting mixture was refluxed with stirring for 2.5 hours. The reaction mixture was cooled and then filtered. The filter cake was washed with ethanol. The filtrate and washing were combined and evaporated under reduced pressure. To the residue was added 5% aqueous solution of potassium hydroxide and the mixture was extracted with chloroform. The extract was washed with water, dried over magnesium sulfate and then evaporated under reduced pressure to give an oil of 3-(4-benzyl-1-piperazinyl)propylamine (12.4 g).

N.M.R. (CDCl$_3$, S): 1.4 (2H, s), 1.6 (2H, tt, J=7 Hz), 2.4 (2H, t, J=7 Hz), 2.47 (8H, s), 2.73 (2H. t, J=7 Hz), 3.5 (2H, s), 7.27 (5H, s).

(3) To a solution of potassium hydroxide (1.3 g) in methanol (9 ml) was added 3-(4-benzyl-1-piperazinyl)propylamine (4.9 g) and thereto was added carbon disulfide (1.8 g) under ice cooling over a period of 10 minutes. The resulting mixture was stirred for 4 hours under ice cooling. The reaction mixture was evaporated under reduced pressure. The residual oil was dissolved in water (20 ml) and washed with diethyl ether. The washed aqueous layer was ice-cooled and thereto was added methyl iodide (3.0 g) with stirring under ice-cooling over a period of 10 minutes. The resulting mixture was stirred for 4 hours under ice-cooling. The reaction mixture was extracted with ethyl acetate, dried over magnesium sulfate and then evaporated under reduced pressure to given an oil of methyl N-[3-(4-benzyl-1-piperazinyl)propyl]dithiocarbamate (4.6 g).

(4) To a solution of methyl N-[3-(4-benzyl-1-piperazinyl)propyl]dithiocarbamate (4.6 g) in a mixture of water (12 ml) and ethanol (8 ml) was added sodium azide (1.2 g). The resulting mixture was refluxed with stirring for 3 hours. The reaction mixture was concentrated under reduced pressure. The concentrate was washed successively with ethyl acetate and diethyl ether and then evaporated. To the residue was added ethanol and the mixture was filtered. The filtrate was evaporated under reduced pressure. To the residue was added 6 N hydrochloric acid. The mixture was evaporated under reduced pressure and the residue was recrystallized from isopropyl alcohol containg water to give 1-[3-(4-benzyl-1-piperazinyl)propyl]-1H-tetrazole-5-thiol dihydrochloride (2.5 g), mp 234° to 237° C.

N.M.R. (DMSO-d$_6$, δ): 2.1–3.0 (2H, m), 3.1–4.1 (10H, m) 4.42 (2H, s), 4.4 (2H, t), 7.3–8.0 (5H, m).

Preparation 3

(1) To the solution of N-(3-bromopropyl)phthalimide (38.8 g) in acetone (400 ml) were added.

1-ally-piperazine (18.5 g) and potassium carbonate (60.8 g). The resulting mixture was refluxed with stirring for 5 hours. The reaction mixture was cooled and then filtered. The filter cake was washed with acetone. The filtrate and washing were combined and evaporated under reduced pressure. The residual oil was subjected to column chromatography on silica gel. The fractions containg the object compound were collected and then evaporated under reduced pressure to give an oil of N-[3-(4-allyl-1-piperazinyl)propyl]phthalimide (35.6 g).

(2) To a solution of N-[3-(4-allyl-1-piperazinyl)propyl]phthalimide (35.6 g) in ethanol (400 ml) was added 100% hydrazine hydrate (14.3 g). The resulting mixture was refluxed with stirring for 2.5 hours. The reaction mixture was cooled and then filtered. The filter cake was washed with ethanol. The filtrate and washing were combined and evaporated under reduced pressure. The residual oil was subjected to column chromatigraphy (aluminum oxide), eluting with a mixture of chloroform and methanol (10:1). The fractions containing the object compound were collected and then evaporated under reduced pressure to give an oil of 3-(4-allyl-1-piperazinyl)propylamine (18.8 g).

N.M.P. (CCl$_4$, δ): 1.43 (2H, s), 1.52 (2H, tt, J=7 Hz), 2.4 (8H, broad s), 2.33 (2H, t, J=7 Hz), 2.67 (2H, t, J=7 Hz), 2.92 (2H, d, J=6 Hz), 5.0–6.0 (3H, m).

(3) To a solution of potassium hydroxide (6.3 g) in methanol (40 ml) was added 3-(4-allyl-1-piperazinyl)propylamine (18.8 g) and thereto was added carbon disulfide (7.8 g) under ice cooling over a period of 10 minutes. The resulting mixture was stirred for 2 hours under ice cooling. The reaction mixture was evaporated under reduced pressure. The residual oil was dissolved in water and washed with diethyl ether. The washed aqueous layer was ice-cooled and thereto was added methyl iodide (14.6 g) with stirring. The resulting mixture was stirred for 2 hours under ice-cooling. The reaction mixture was extracted with ethyl acetate, the extract was washed with a saturated aqueous solution of sodium chloride, dried over magnesium sulfate and then evaporated under reduced pressure to give an oil of methyl N-[3-(4-allyl-1-piperazinyl)propyl]dithiocarbamate (17.7 g).

(4) To a solution of methyl N-[3-(4-allyl-1-piperazinyl)propyl]dithiocarbamate (17.7 g) in a mixture of water (60 ml) and ethanol (40 ml) was added sodium azide (5.5 g). The resulting mixture was refluxed with stirring for 3 hours. The reaction mixture was concentrated under reduced pressure. The concentrate was washed successively with ethyl acetate and diethyl ether and then evaporated. To the residue was added ethanol and the mixture was filtered. The filtrate was evaporated under reduced pressure. To the residue was added 6 N hydrochloric acid. The mixture was evaporated under reduced pressure. The residue was recrystallized from methanol containing water to give 1-[3-(4-allyl-1-piperazinyl)propyl]-1H-tetrazole-5-thiol dihydrochloride (2.5 g), mp 211° to 215° C. (dec.)

N.M.R. (D$_2$O, δ): 2.2–2.8 (2H, m), 3.78 (8H, s), 3.67 (2H, t, J=6 Hz) 3.97 (2H, d, J=7 Hz), 4.50 (2H, t, J=7 Hz), 5.5–6.5 (3H, m).

Preparation 4

(1) To the solution of N-(3-bromopropyl)phthalimide (40.5 g) in acetone (375 ml) were added 1-(2-hydroxyethyl)piperazine (31.5 g) and potassium carbonate (63.0 g). The resulting mixture was refluxed with stirring for 3 hours. The reaction mixture was filtered and the filtrate was evaporated. The residual oil was subjected to column chromatography on silica gel, eluting with a mixture of chloroform and methanol (9:1). The fractions containing the object compound were collected and then evaporated to give an oil of N-[3-[4-(2-hydroxyethyl)-1-piperazinyl]propyl]phthalimide (25.5 g).

(2) To a solution of N-[3-[4-(2-hydroxyethyl)-1-piperazinyl]propyl]phthalimide (14.4 g) in ethanol (145 ml) was added 100% hydrazine hydrate (6.6 g). The resulting mixture was refluxed with stirring for 2 hours. The reaction mixture was cooled and then filtered. The filter cake was washed with ethanol. The filtrate and washing were combined and evaporated under reduced pressure. The residual oil was subjected to column chromatography (Aluminum oxide), eluting with a mixture of chloroform and methanol (20:1). The fractions containing the object compound were collected and then evaporated to give an oil of 3-[4-(2-hydroxyethyl)-1-piperazinyl)]propylamine (5.0 g).

N.M.R. (DMSO-d$_6$, S) 1.48 (2H, tt, J=7 Hz), 2.28 (2H, t, J=7 Hz), 2.53 (2H, t, J=7 Hz), 2.1–2.7 (10H, m), 3.03 (3H, s), 3.16 (2H, t, J=7 Hz).

(3) To a solution of potassium hydroxide (1.5 g) in methanol (11 ml) was added 3-[4-(2-hydroxyethyl)-1-piperazinyl]propylamine (5.0 g) and thereto was added carbon disulfide (2.0 g) under ice cooling over a period of 10 minutes. The resulting mixture was stirred for 2 hours under ice cooling. The reaction mixture was evaporated under reduced pressure. The residual oil was dissolved in water (10 ml), washed with diethyl ether. The washed aqueous layer was ice-cooled and thereto was added methyl iodide (3.8 g) with stirring. The resulting mixture was stirred for 2 hours under ice-cooling, extracted with ethyl acetate, dried over magnesium sulfate and then evaporated to give methyl N-[3-[4-(2-hydroxy-ethyl)-1-piperazinyl]propyl]dithiocarbamate (4.8 g).

(4) To a solution of methyl N-[3-[4-(2-hydroxyethyl)-1-piperazinyl]-propyl]-dithiocarbamate (4.8 g) in a mixture of water (15 ml) and ethanol (10 ml) was added sodium azide (1.5 g). The resulting mixture was refluxed with stirring for 4 hours. The reaction mixture was concentrated under reduced pressure. The concentrate was disolved in water and the solution was washed successively with ethyl acetate and diethyl ether and then evaporated. To the residue was added ethanol and the mixture was filtered. The filtrate was evaporated under reduced pressure. The residue was recrystallized from isopropyl alcohol to give 1-[3-[4-(2-hydroxyethyl)-1-piperazinyl]propyl]-1H-tetrazole-5-thiol (1.35 g).

N.M.R. (D$_2$O, δ): 2.0–3.0 (14H, m), 3.79 (2H, t, J=7 Hz), 4.40 (2H, t, J=7 Hz).

Preparation 5

(1) To the solution of N-(3-bromopropyl)phthalimide (53.0 g) in acetone (400 ml) were added.

1-ethoxycarbonyl piperazine (50.0 g) and potassium carbonate (82.0 g). The resulting mixture was refluxed with stirring for 15 hours. The reaction mixture was cooled and then filtered. The filter cake was washed with acetone. The filtrate and washing were combined and evaporated under reduced pressure. The residue was recrystallized from a mixture of benzene and n-hexane to give N-[3-(4-ethoxycarbonyl-1-piperazinyl)propyl]phthalimide (65.2 g), mp 77° to 84° C.

(2) To a solution of N-[3-(4-ethoxycarbonyl-1-piperazinyl)propyl]phthalimide (28.9 g) in ethanol (300 ml) was added 100% hydrazine hydrate (8.4 g). The resulting mixture was refluxed with stirring for 4 hours. The reaction mixture was cooled and then filtered. The filter cake was washed with ethanol. The filtrate and washing were combined and evaporated. Under reduced pressure. After the addition of an aqueous solution of sodium hydroxide to the residue, the mixture was extracted with chloroform The extract was washed with water, dried over magnesium sulfate and then evaporated under reduced pressure to give an oil of 3-(4-ethoxycarbonyl-1-piperazinyl)propylamine (10.9 g).

N.M.R. (CDCl$_3$, $\delta$): 1.27 (3H, t, J=7 Hz), 1.63 (2H, tt, J=7 Hz), 2.3–2.6 (6H, m), 2.80 (2H, t, J=7 Hz), 3.4–3.7 (4H, m), 4.17 (2H, q, J=7 Hz).

(3) To a solution of potassium hydroxide (2.9 g) in methanol (40 m) was added 3-(4-ethoxycarbonyl-1-piperazinyl)propylamine (10.9 g) and thereto was added carbon disulfide (3.9 g) under ice cooling over a period of 5 minutes. The resulting mixture was stirred for 4 hours under ice cooling. The reaction mixture was evaporated under reduced pressure. The residual oil was dissolved in water (40 ml) and washed with diethyl ether. The washed aqueous layer was ice-cooled and thereto was added methyl iodide (7.2 g) with stirring. The resulting mixture was stirred for 2 hours under ice-cooling, and extracted with ethyl acetate. The extract was dried over magnesium sulfate and then evaporated under reduced pressure to give an oil of methyl N-[3-(4-ethoxy-carbonyl-1-piperazinyl)propyl]dithiocarbamate (11.7 g).

(4) To a solution of methyl N-[3-(4-ethoxy-carbonyl-1-piperazinyl)propyl]dithiocarbamate (11.7 g) in a mixture of water (40 ml) and ethanol (30 ml) was added sodium azide (3.3 g). The resulting mixture was refluxed with stirring for 4 hours. The reaction mixture was concentrated under reduced pressure. After the addition of water to the residue, the mixture was washed with diethyl ether and then evaporated. To the residue was added ethanol and the mixture was filtered. The filtrate was evaporated under reduced pressure. After the addion of a mixture of hydrochloric acid and ethanol to the residue, the resulting mixture was evaporated under reduced pressure. The residue was triturated with acetone to give crude crystals of the object compound (5.7 g), which were recrystallized from ethanol to give 1-[3-(4-ethoxycarbonyl-1-piperazinyl)propyl]-1H-tetrazole-5-thiol hydrochloride (2.1 g), mp 192° to 197° C. (dec.).

N.M.R. (DMSO-d$_6$, $\delta$): 1.22 (3H, t, J=7 Hz), 2.1–2.5 (2H, m), 3.0–3.5 (6H, m), 3.5–3.9 (4H, m), 4.13 (2H, q, J=7 Hz), 4.37 (2H, t, J=7 Hz).

Preparation 6

(1) To the solution of N-(3-bromopropyl)phthalimide (30.1 g) in acetone (200 ml) were added 1-isopropylpiperazine (23.0 g) and potassium carbonate (41.4 g). The resulting mixture was refluxed with stirring for 4 hours. The reaction maxture was cooled and then filtered. The filter cake was washed with acetone. The filtrate and washing were combined and evaporated under reduced pressure to give an oil of N-[3-(4-iospropyl-1-piperazinyl)propyl]phthalimide (43.5 g).

(2) To a solution of N-[3-(4-isopropyl-1-piperazinyl)propyl]phthalimide (43.1 g) in ethanol (350 ml) was added 100% hydrazine hydrate (11.2 g). The resulting mixture was refluxed with stirring for 3 hours. The reaction mixture was cooled and then filtered. The filter cake was washed with ethanol. The filtrate and washing were combined and concentrated under reduced pressure. The residual oil was subjected to column chromatography (aluminum oxide), eluting with a mixture of chloroform and methanol (20:1). The fractions containing the object compound were collected and then evaporated under reduced pressure. The residual oil was distilled under reduced pressure to give 3-(4-isopropyl-1-piperazinyl)propylamine (15.0 g), (bp 45 mmHg/150° C.).

(3) To a solution of potassium hydroxide (4.9 g) in methanol (40 ml) was added 3-(4-isopropyl-1-piperazinyl)propylamine (14.7 g) and thereto was added carbon disulfide (6.0 g) under ice cooling over a period of 20 minutes. The resulting mixture was stirred for 3.5 hours under ice cooling. The reaction mixture was evaporated under reduced pressure. The residual oil was dissolved in water (40 ml) and washed with diethyl ether. The washed aqueous layer was ice-cooled and thereto was added methyl iodide (11.3 g) with stirring over a period of about 5 minutes. The resulting mixture was stirred for 2 hours under ice-cooling extracted with chloroform. The extract was washed with water, dried over magnesium sulfate and then evaporated to give an oil of methyl N-[3-(4-isopropyl-1-piperazinyl)propyl]dithiocarbamate (15.6 g).

(4) To a solution of methyl N-[3-(4-isopropyl-1-piperazinyl)propyl]dithiocarbamate (15.1 g) in a mixture of water (50 ml) and ethanol (40 ml) was added sodium azide (4.6 g). The resulting mixture was refluxed with stirring for 4.5 hours. The reaction mixture was concentrated under reduced pressure. The concentrate was washed successively with diethyl ether and ethyl acetate and then evaporated. To the residue was added ethanol and the mixture was filtered. The filtrate was evaporated under reduced pressure. After the addition of a little amount of mixture of hydrochloric acid and ethanol to the residual oil, the product was recrystallized from methanol to give 1-[3-(4-isopropyl-1-piperazinyl)propyl]-1H-tetrazole-5-thiol dihydrochloride (3.6 g).

N.M.R. (DMSO-d$_6$, $\delta$): 1.28 (6H, d, J=6 Hz), 2.1–2.5 (2H, m), 3.1–3.8 (3H, m), 3.58 (8H, s), 4.33 (2H, t, J=8 Hz).

Preparation 7

(1) To the solution of N-(3-bromopropyl)phthalimide (15.6 g) in acetone (150 ml) were added 1-phenylpiperazine (10.4 g) and potassium carbonate (12.0 g). The resulting mixture was refluxed with stirring for 4.5 hours. The reaction mixture was cooled and then filtered. The filter cake was washed with acetone. The filtrate and washing were combined and evaporated under reduced pressure. The residue was recrystallized from ethanol to give an oil of N-[3-(4-phenyl-1-piperazinyl)propyl]phthalimide (18.3 g), mp 129° to 134° C.

(2) To a solution of N-[3-(4-phenyl-1-piperazinyl)propyl]phthalimide (18.3 g) in ethanol (300 ml) was added 100% hydrazine hydrate (5.3 g). The resulting mixture was refluxed with stirring for 2 hours. The reaction mixture was evaporated under reduced pressure. After the addition of dil. aqueous solution of sodium hydroxide to the residue, the mixture was extracted with chloroform. The extract was washed with water, dried over magnesium sulfate and then evaporated under reduced pressure to give 3-(4-phenyl-1-piperazinyl)propylamine (11.2 g).

N.M.R. (CCl$_4$ δ): 1.47 (2H, broad s), 1.57 (2H, tt, J=7 Hz), 2.38 (2H, t, J=7 Hz), 2.72 (2H, t, J=7 Hz), 2.4–2.7 (4H, m), 3.0–3.2 (4H, m), 6.6–7.4 (5H, m).

(3) To a solution of potassium hydroxide (2.85 g) in methanol (25 ml) was added 3-(4-phenyl-1-piperazinyl)-propylamine (11.1 g) and thereto was added carbon disulfide (3.85 g) under ice cooling over a period of 10 minutes. The resulting mixture was stirred for 3 hours under ice cooling. The reaction mixture was evaporated under reduced pressure. The residual oil was dissolved in water (40 ml) and washed with diethyl ether. The washed aqueous layer was ice-cooled and thereto was added methyl iodide (7.2 g) with stirring. The resulting mixture was stirred for 2 hours under ice-cooling and extracted with ethyl acetate. The extract was washed with water, dried over magnesium sulfate and then evaporated to give methyl N-[3-(4-phenyl-1-piperazinyl)propyl]dithiocarbamate (12.9 g), mp 75° to 79° C.

(4) To a solution of methyl N-[3-(4-phenyl-1-piperazinyl)propyl]dithiocarbamate (12.9 g) in a mixture of water (20 m) and ethanol (30 m) was added sodium azide (3.6 g). The resulting mixture was refluxed with stirring for 4.5 hours. The reaction mixture was concentrated under reduced pressure. After the addition of water to the residue, the mixture was washed successively with ethyl acetate and diethyl ether and then evaporated. To the residue was added ethanol (100 m) and the mixture was filtered. The filtrate was evaporated under reduced pressure. The residue was recrystallized from isopropyl alcohol twice to give 1-[3-(4-phenyl-1-piperazinyl)propyl]-4,5-dihydro-1H-tetrazole-5-thione (3.2 g), mp. 200° to 205° C.

I.R. (Nujol): 3270, 1600 cm$^{-1}$.

N.M.R. (DMSO-d$_6$, δ): 1.8–2.1 (2H, m), 3.0–3.2 (4H, m), 4.17 (2H, t, J=6 Hz), 6.8–7.5 (5H, m).

A solution of the above obtained product in a little amount of water was acidified with dil hydrochloric acid and then adjusted to pH 7.0 with an aqueous solution of sodium bicarbonate. The precipitates were collected by filtration, washed with water and dried to give 1-[3-(4-phenyl-1-piperazinyl)propyl]-1H-tetrazole-5-thiol, mp 220° to 233° C. (dec.).

I.R. (Nujol): 2350, 1590 cm$^{-1}$.

N.M.R. (DMSO-d$_6$, δ): 2.0–2.3 (2H, m), 4.3 (2H, t, J=6 Hz), 6.8–7.5 (5H, m).

Preparation 8

The following compounds were prepared according to the similar manners to those of Preparation 1–7.

(1) 1-[2-(4-Methyl-1-piperazinyl)ethyl]-1H-tetrazole-5-thiol.hydrobromide, mp 216° to 222° C., N.M.P. (D$_2$O, δ): 2.80 (3H, s), 2.80 (4H, m), 3.04 (2H, t, J=6 Hz), 3.28 (4H, m), 4.48 (2H, t, J=6 Hz).

(2) 1-(4-Methyl-1-piperazinyl)carbonylmethyl)-1H-tetrazole-5-thiol, mp>250° C.

| Elemental Analysis | C | H | N |
|---|---|---|---|
| Calcd | 39.65 | 5.82 | 34.69 |
| Found | 39.33 | 5.68 | 34.52 |

Preparation 9

(1) A mixture of 4-(2-hydroxyethyl) thiosemicarbazide (10.3 g), benzyl chloride (10.6 g), water (30 ml) and methanol (60 ml) was stirred for 20 hours at room temperature to give a homogeneous solution containing benzyl N-(2-hydroxyethyl) thiocarbazimidate. The solution was ice-cooled and thereto was little by little added sodium nitrate (5.24 g) with stirring and then dropwise added conc. hydrochloric acid (3.5 ml) over a period of 30 mimetes. The resulting mixture was stirred for an hour under ice-cooling. To the reaction mixture were added potassium carbonate (18 g) and water (30 ml). The mixture was stirred and then concentrated under reduced pressure. The concentrate was extracted with chloroform and the extract was washed with water, dried over magnesium sulfate and then evaporated under reduced pressure. The residual oil was subjected to column chromatography on silica gel. The fractions containing the object compound were collected to give an oil of 1-(2-hydroxyethyl)-5-benzylthio-1H-tetrazole (12.1 g).

I.R. (Film): 3380, 1595, 1490 cm$^{-1}$.

N.M.R. (CDCl$_3$, δ): 3.1 (1H, m), 4.1 (2H, m), 4.23 (2H, m), 4.50 (2H, s), 7.33 (5H, s).

(2) To a solution of 1-(2-hydroxyethyl)-5-benzylthio-1H-tetrazole (7.0 g) in pyridine (50 ml) was added p-toluenesulfonyl chloride (6.3 g) and the mixture was stirred for 3 hours. After the addition of water, the reaction mixture was extracted with ethyl acetate. The extract was washed with water, dried over magnesium sulfate and then concentrated under reduced pressure. To the residual oil containing 1-(2-tosyloxyethyl)-5-benzylthio-1H-tetrazole were added 1-methylpiperazine (12.0 g), potassium carbonate (12.2 g) and N.N-dimethylformamide (55 m) and the mixture was stirred for 5 hours at 50° C. After the addition of water, the reaction mixture was extracted with ethyl acetate. The extract was washed with water, dried over magnesium sulfate and evaporated under reduced pressure. The crude product was subjected to column chromatography on silica gel. The fractions containing the object compound was collected to give an oil of 1-[2-(4-methyl-1-piperazinyl)ethyl]-5-benzylthio-1H-tetrazole (6.5 g).

I.R. (Film): 1600, 1498, 1460, 1164 cm$^{-1}$.

N.M.R. (CDCl$_3$, δ): 2.23 (3H, s), 2.1–2.7 (8H, m), 2.7 (2H, t, J=6.0 Hz), 4.17 (2H, t, J=6.0 Hz), 4.5 (2H, s), 7.27 (5H, s).

(3) A mixture of 1-[2-(4-methyl-1-piperazinyl)ethyl]-5 benzylthio-1H-tetrazole (5.4 g), acetic acid (40 ml) and conc. hydrobromic acid (40 ml) was heated at 70° to 80° C. for 8 hours. After the concentration of the reaction mixture, the concentrate was diluted with water. The mixture was washed with diethyl ether twice and evaporated under reduced pressure. The residue was recrystallized from methanol. A solution of the obtained crystals in a little amounted of water was adjusted to pH 6.0 with 1 N aqueous solution of potassium hydroxide., washed with ethyl acetate and then evaporated under reduced pressure. To the residue was added hot ethanol and insoluble materials were filtered out. The filtrate was cooled and the precipitated crystals were collected by filtration to give 1-[2-(4-methyl-1-piperazinyl)ethyl]-1H-tetrazole-5-thiol hydrobromide (1.1 g), mp 216° to 222° C.

N.M.R. (D$_2$O, δ): 2.80 (3H, s), 280 (4H. m), 3.04 (2H, t, J=6 Hz), 3.28 (4H, m), 4.48 (2H, t, J=6 Hz).

Preparation 10

The following compounds were prepared according to the similar manner to that of Preparation 9.

(1)   1-[3-(4-Methyl-1-piperazinyl)propyl]-1H-tetrazole-5-thiol.dihydrochloride, mp 239° to 243° C.

(2)   1-[3-(4-Benzyl-1-piperazinyl)propyl]-1H-tetrazole-5-thiol.dihydrochloride, mp 234° to 237° C.

(3)   1-[3-(4-Allyl-1-piperazinyl)propyl]-1H-tetrazole-5-thiol.dihydrochloride, mp 211° to 215° C. (dec.)

(4)   1-[3-[4-(2-hydroxyethyl)-1-piperazinyl]propyl]-1H-tetrazole-5-thiol.

N.M.R. (D$_2$O, δ): 2.0–3.0 (14H, m), 3.79 (2H, t, J=7 Hz), 4.40 (2H, t, J=7 Hz).

(5)   1-[3-(4-Ethoxycarbonyl-1-piperazinyl)propyl]-1H-tetrazole-5-thiol, mp 192° to 197° C. (dec.).

(6)   1-[3-(4-Isopropyl-1-piperazinyl)propyl]-1H-tetrazole-5-thiol.dihydrochloride.

N.M.R. (DMSO-d$_6$): 1.28 (6H, d, J=6 Hz), 2.1–2.5 (2H, m), 3.1–3.8 (3H, m), 3.58 (8H, s), 4.33 (2H, t, J=8 Hz).

(7)   1-[3-(4-Phenyl-1-piperazinyl)propyl]-1H-tetrazole-5-thiol, mp 220° to 223° C. (dec.).

(8)   1-(4-Methyl-1-piperazinyl)carbonylmethyl-1H-tetrazole-5-thiol, mp>250° C.

Preparation 11

To a solution of 1-carboxymethyl-1H-tetrazole-5-thiol (3.2 g) in dry acetone (60 ml) was added triethyl amine (4.2 g). After the addition of a solution of pivaloyl chloride (4.8 g) in dry acetone (10 ml) with stirring at −15° C. over a period of 5 minutes, the mixture was stirred for one hour and 15 minutes at the same temperature. A solution of 1-methylpiperazine (4.0 g) in dry acetone (10 ml) was dropwise added over a period of 5 minutes and the resulting mixture was stirred at −15° C. for 40 minutes and under ice-cooling for a further 2.5 hours. After the evaporation of the reaction mixture under reduced pressure, water was added to the residue, 4 N aqueous solution of sodium hydroxide was added until the crystals were dissolved. The resulting solution was evaporated under reduced pressure and the residue was crystallized from water to give 1-(4-methyl-1-piperazinyl) carbonylmethyl-1H-tetrazole-5-thiol (2.2 g). mp>250° C.

| Elemental Analysis | C | H | N |
| --- | --- | --- | --- |
| Calcd. | 39.65 | 5.82 | 34.69 |
| Found. | 39.33 | 5.68 | 34.52 |

Preparation 12

(1) To a solution of benzhydryl 2-carboxy-2-(4-benzyloxyphemyl) acetate (10 g) in methylene chloride (70 ml) precooled at 0° C. was added oxalyl chloride (1.54 ml) and the mixture was stirred for 30 minutes at 0° C. The resulting mixture was dropwise added to a mixture of benzhydryl 7α-methoxy-7β-amino-cephalosporanate (8.5 g), pyridine (1.46 ml) and methylene chloride (80 ml) over a period of about 2 minutes keeping the temperature below 4° C. and then the mixture was stirred for 1.5 hours at 0° C. The reaction mixture was concentrated and to the concentrate were added water and ethyl acetate. The ethyl acetate layer was separated and thereto was added water. The mixture was adjusted to pH 1 with dil. hydrochloric acid and to the separated ethyl acetate layer was added water. The resulting mixture was adjusted to pH 8 with an aqueous solution of sodium bicarbonate. The ethyl acetate layer was separated, washed with a saturated aqueous solution of sodium chloride dried over magnesium sulfate and then filtered. The filtrate was evaporated to give a dark brown solid (15.7 g). A solution of the solid in methylene chloride was subjected to column chromatography (silica gel: 235 g), eluting with methylene chloride. The fractions containing the object compound were collected and then concentrated. The residual oil was pulverized in diisopropyl ether to give a powder of benzhydryl 7α-methoxy-7β-[2-benzhydryloxycarbonyl-2-4-(4-benzyloxyphenyl)acetamido]cephalosporanate (4.0 g)

I.R. (Nujol): 3350, 1780, 1740, 1610, 1510 cm$^{-1}$.

N.M.R. (DMSO-d$_6$, δ): 1.98 (3H, s), 3.30 (3H, s), 3.42 (2H, broad s), 4.6–4.9 (2H, broad s), 5.13 (3H, s), 5.24 (1H, s), 6.8–7.6 (31H, m).

(2) To a solution of benzhydryl 7α-methoxy-7β-[2-benzhydryloxycarbonyl-2-(4-benzyloxyphenyl)acetamido]cephalosporanate (1.5 g), anisole (3.6 ml) in methylene chloride (15 ml) was dropwise added a solution of aluminum chloride (2.21 g) in methyl nitrite (13 ml) over a period of 5 minutes and the mixture was stirred for 1 hour and 40 minutes under ice-cooling. After the addition of water and ethyl acetate to the reaction mixture, the ethyl acetate layer was separated and thereto was added water. The mixture was adjusted to pH7 with an aqueous solution of sodium bicarbonate and then poured into water. The aqueous layer was separated and thereto was added ethyl acetate. The mixture was adjusted to pH1 with dil. hydrochloric acid and the ethyl acetate layer was separated, dried over magnesium sulfate and then filtered. The filtrate was concentrated and the concentrate was pulverized in diisopropyl ether to give 7α-methoxy-7β-[D,L-2-carboxy-2-(4-hydroxyphenyl)acetamido]cephalosporanic acid (0.7 g).

I.R. (KBr): 3250, 3000, 1770, 1720, 1610, 1510, 1440, 1380 cm$^{-1}$.

N.M.R. (DMSO-d$_6$, δ): 2.0 (3H, s), 3.42 (3H, s), 3.3–3.6 (2H, m), 4.70 (1H, s), 4.6–4.9 (2H, m), 5.07 (1H, s), 6.67, 7.13 (4H, ABq, J=8 Hz), 9.4 (1H, broad s).

EXAMPLE 1

To a solution of 1-[3-(4-methyl-1-piperazinyl)propyl]-1H-tetrazole-5-thiol.dihydrochloride (75.32 g) in water (6 l) was added 7-aminocephalosporanic acid (60.0 g) and the mixture was adjusted to pH 5.4 with a saturated aqueous solution of sodium bicarbonate and stirred for 2 hours at 64° C. The reaction mixture was cooled and adjusted to pH 6.84 with a saturated aqueous solution of sodium bicarbonate. The resulting mixture was subjected to column chromatography (CM-Cephadex, H-type: 3 l), eluting with water, 0.5% aqueous solution of sodium chloride and 2% aqueous solution of sodium chloride. The fiactions containing the object compound were collected. The resulting mixture (about 7 l) was adjusted to pH 4.5 with a saturated aqueous solution of sodium bicarbonate and then subjected to column chromatography (Non-ion adsorption resin, Diaion HP 20 prepared by Mitsubishi Chemical Industries: 3 l) and eluting with water, 2% isopropyl alcohol and 15% isopropyl alcohol. The fractions containing the object compound were collected and then concentrated. The concentrate was lyophilized to give a powder of 7-amino-3-[1-[3-(4-methyl-1-piperazinyl) propyl]-1H-tetrazol-5-yl]thiomethyl-3-cephem-4-carboxylic acid (34.6 g).

I.R. (KBr): 3400, 1760, 1600 cm$^{-1}$.

N.M.R. (D$_2$O, δ); 2.30 (2H, m), 2.5–3.5 (10H, m), 2.90 (3H, s), 3.57, 3.83 (2H, ABq, J=18 Hz), 4.20, 4.40 (2H, ABq, J=14 Hz), 4.52 (2H, t, J=7 Hz), 4.88 (1H, d, J=5 Hz), 5.13 (1H, d, J=5 Hz).

EXAMPLE 2

A solution of 7-[2-methoxyimino-2-(2-aminothizol-4-yl)acetamido] cephalosporanic acid (syn isomer) (20.0 g) and 1-[3-(4-methyl-1-piperazinyl)propyl]-1H-tetrazole-5-thiol.dihydrochloride (16.6 g) in water (1 l) was adjusted to pH 6.0 with a saturated aqueous solution of sodium bicarbonate. The mixture was stirred for 3 hours and 20 minutes at 63° to 65° C. while the pH was maintained at 6.0 to 6.2 with 5% hydrochloric acid. The reaction mixture was ice-cooled and adjusted to pH 7.3 with a saturated aqueous solution of sodium bicarbonate and thereto was added cold water (3 l). The resulting solution was subjected to column chromatograph (CM-Cephadex, H-type: 1 l), eluting with water (200 ml), 1% (2 l), 2% (2 l) and 4% (4 l) aqueous solution of sodium chloride. The fractions containing the object compound were collected. The resulting mixture (about 2 l) was adjusted to pH 4.5 with a saturated aqueous solution of sodium bicarbonate and subjected to column chromatography (Non ion adsorption resin, Diaion HP 20 prepared by Mitsubishi Chemical Industries: 500 ml), eluting with water (0.5 l), 5% (1 l) and 15% (2.5 l) isopropyl alcohol. The fractions containing the object compound were collected and then concentrated. The concentrate was lyophilized to give 7-[2-methoxyimino-2-(2-aminothiazol-4-yl)acetamido]-3-[1-[3-(4-methyl-1-piperazinyl)propyl]-1H-tetrazol-5-yl]thiomethyl-3-cephem-4-carboxylic acid (syn isomer). (9.2 g).

I.R. (Nujol): 3300, 1760, 1660, 1600, 1530 cm$^{-1}$.

N.M.R. (DMSO-d$_6$, δ): 2.0 (2H, m), 2.3–3.0 (10H, m), 2.55 (3H, s), 3.47, 3.73 (2H, ABq J=18 Hz), 3.84 (3H, s), 4.32 (4H, broad s), 5.05 (1H, d, J=5 Hz), 5.67 (1H, dd, J=5 and 8 Hz), 6.75 (1H, s), 7.22 (2H, broad s), 9.51 (1H, d, J=8 Hz).

EXAMPLE 3

A mixture of 7-[2-methoxyimino-2-(2-aminothiazol-4-yl)acetamido]cephalosporanic acid (syn isomer) (1.2 g), 1-[2-(4-methyl-1-piperazinyl)ethyl]-1H-tetrazole-5-thiol.hydrobromide (1.2 g) and phosphate buffer (PH6.4: 100 ml) was adjusted to pH 6.7 with a saturated aqueous solution of sodium bicarbonate. The mixture was stirred for 6 hours at 65° C., cooled to room temperature and then adjusted to pH 4.5 with 5% hydrochloric acid. The resulting mixture was subjected to column chromatography (Non-ion adsorption resin, Diaion HP20 prepared by Mitsubishi Chemical Industries: 60 ml), eluting with water, 5%, 10% and 20% isopropyl alcohol. The fractions containing the object compound were collected, and then concentrated. The concentrate was lyophilized to give powder of 7-[2-methoxyimino-2-(2-aminothiazol-4-yl) acetamido]-3-[1-]2-(4-methyl-1-piperazinyl)ethyl]-1H-tetrazol-5-yl]thiomethyl-3-cephem-4-carboxylic acid (syn isomer) (0.70 g).

I.R. (Nujol): 3300, 1765, 1660, 1600, 1530 cm$^{-1}$.

N.M.R. (DMSO-d$_6$, δ): 2.5–3.1 (10H, m), 2.60 (3H, s), 3.63 (2H, broad s), 3.87 (3H, s), 4.47 (4H, broad s), 5.08 (1H, d, J=5 Hz), 5.70 (1H, dd, J=5 and 8 Hz), 6.77 (1H, s), 7.23 (2H, broad s), 9.56 (1H, d, J=8 Hz).

EXAMPLE 4

A mixture of 7-[2-methoxyimino-2-(2-aminothiazol-4-yl)acetamido]cephalosporanic acid (syn isomer) (1.5 g), 1-(4-methyl-1-piperazinyl)carbonylmethyl-1H-tetrazole-5-thiol (1.03 g), phosphate buffer (pH 6.4, 50 ml) and water (50 ml) was adjusted to pH 7.0 with a saturated aqueous solution of sodium bicarbonate and the mixture was stirred for 5 hours and 50 minutes at 60° C. The reaction mixture was cooled and adjusted to pH 4.5 with 5% hydrochloric acid. The resulting mixture was subjected to column chromatography (Non-ion adsorption resin, Diaion HP20 prepared by Mitsubishi Chemical Industries: 75 ml), eluting with water, 5% and 10% isopropyl alcohol. The fractions containing the object compound were collected and concentrated. The concentrate was lyophilized to give a powder of 7-[2-methoxyimino-2-(2-aminothiazol-4-yl)acetamido]-3-[1-(4-methyl-1-piperazinyl)carbonylmethyl-1H-tetrazol-5-yl]thiomethyl-3-cephem-4-carboxylic acid (syn isomer).

I.R. (Nujol): 3300, 1760, 1660, 1600, 1530 cm$^{-1}$.

N.M.R. (DMSO-d$_6$, δ): 2.5 (3H, s), 2.5–3.0 (4H, m), 3.4–3.9 (6H, m), 3.82 (3H, s), 4.27 (2H, broad s), 5.08 (1H, d, J=5 Hz), 5.57 (2H, broad s), 5.65 (1H, dd, J=5 and 8 Hz), 6.75 (1H, s), 7.17 (2H, broad s), 9.55 (1H, d, J=5 Hz).

EXAMPLE 5

A solution of 7α-methoxy-7β-[D,L-2-carboxy-2-(4-hydroxyphenyl)acetamido]cephalosporanic acid (0.28 g), 1-[3-(4-methyl-1-piperazinyl)propyl]-1H-tetrazole-5-thiol.dihydrochloride (1.3 g) in phosphate buffer (pH 6.4: 100 ml) was stirred for 2 hours and 50 minutes at 65° C. The reaction mixture was adjusted to pH 4.5 with 6 N hydrochloric acid and then subjected to column chromatography (Non-ion adsorption resin, Diaion HP-20 prepared by Mitsubishi Chemical Industries: 50 ml), eluting with water (50 ml), 3% (100 ml), 4% (100 ml) and 25% (200 ml) isopropyl alcohol. The fractions containing the object compound were collected and concentrated. The concentrate was lyophilized to give a powder of 7α-methoxy-7β-[D,L-2-carboxy-2-(4-hydroxyphenyl)acetamido]-3-[3-(4-methyl-1-piperazinyl)propyl]-1H-tetrazol-5-yl]thiomethyl-3-cephem-4-carboxylic acid (0.15 g).

I.R. (Nujol): 3200, 1760, 1670, 1600, 1505 cm$^{-1}$.

N.M.R. (D$_2$O-N$_a$HCO$_3$, δ): 2.5–3.2 (12H, m), 2.75 (3H, s), 3.5 (3H, s) 3.6 (2H, broad s), 4.2–4.6 (4H, m), 5.13, 5.16 (1H, each s), 5.35 (1H, s), 6.97, 7.40 (4H, ABq, J=8 Hz).

EXAMPLE 6

The following compounds were prepared according to the similar manners to those of Examples 1 to 5.

(1) 7-[2-methoxyimino-2-(2-aminothiazol-4-yl) acetamido]-3-[1-[3-(4-isopropyl-1-piperazinyl)propyl]-1H-tetrazol-5-yl]thiomethyl-3-cephem-4-carboxylic acid (syn isomer), powder.

I.R. (Nujol): 3300, 1765, 1660, 1600, 1530 cm$^{-1}$.

N.M.R. (DMSO-d$_6$): 1.22 (6H, d, J=6 Hz), 2.0 (2H, m), 2.3–3.1 (11H, m), 3.87 (3H, s), 4.37 (4H, broad s), 5.10 (1H, d, J=5 Hz), 5.73 (1H, dd, J=5 and 8 Hz), 6.77 (1H, s), 7.23 (2H, broad s), 9.57 (1H, d, J=8 Hz).

(2) Sodium 7-[2-methoxyimino-2-(2-aminothiazol-4-yl) acetamido]-3-[1-[3-(4-benzyl-1-piperazinyl)propyl]-1H-tetrazol-5-yl]thiomethyl-3-cephem-4-carboxylate (syn isomer), powder.

I.R. (Nujol): 3300, 1760, 1660, 1600 cm$^{-1}$.

N.M.R. (DMSO-d$_6$, δ): 2.0 (2H, m), 2.5–2.8 (10H, broad s), 3.60 (2H, broad s), 3.73 (2H, broad s), 3.86 (3H, s), 4.30 (4H, broad s), 5.10 (1H, d, J=5 Hz), 5.74 (1H, dd, J=5 and 8 Hz), 6.77 (1H, s), 7.40 (7H, broad s), 9.56 (1H, d, J=8 Hz).

(3) Sodium 7-[2-methoxyimino-2-(2-aminothiazol-4-yl) acetamido]-3-[1-[3-(4-allyl-1-piperazinyl)propyl]-1H-tetrazol-5-yl]thiomethyl-3-ceplem-4-carboxylate (syn isomer), powder.

I.R. (Nujol): 3350, 1770, 1670, 1600, 1530 cm$^{-1}$.

N.M.R. (DMSO-d$_6$, δ): 3.83 (3H, s), 5.00 (1H, d, J=5 Hz), 6.73 (1H, s), 7.20 (2H, broad s), 9.50 (1H, d, J=8 Hz).

(4) Sodium 7-[2-methoxyimino-2-(2-aminothiazol-4-yl) acetamido]-3-[1-[3-(4-phenyl-1-piperazinyl)propyl]-1H-tetrazol-5-yl]thiomethyl-3-cephem-4-carboxylate (syn isomer), powder.

I.R. (Nujol): 3300, 1765, 1665, 1600, 1530 cm$^{-1}$.

N.M.R. (DMSO-d$_6$, δ): 2.1 (2H, m), 2.5–3.4 (10H, m), 3.63 (2H, broad s), 3.80 (3H, s), 4.25 (2H, broad s), 4.33 (2H, broad s), 5.05 (1H, d, J=5 Hz), 5.70 (1H, dd, J=5 and 8 Hz), 6.68 (1H, s), 6.7–7.3 (7H, m), 9.48 (1H, d, J=8 Hz).

(5) 7-[2-methoxyimino-2-(2-aminothiazol-4-yl)acetamido]-3-[1-[3-[4-(2-hydroxyethyl)-1-piperazinyl]propyl]-1H-tetrazol-5-yl]thiomethyl-3-cephem-4-carboxylic acid (syn isomer), powder.

I.R. (Nujol): 3350, 3250, 1775, 1670, 1610, 1540 cm$^{-1}$.

N.M.R. (DMSO-d$_6$, δ): 1.9–2.1 (2H, m), 2.3–3.0 (12H, m), 3.62 (4H, broad s), 3.80 (3H, s), 4.30 (4H, broad s), 5.00 (1H, d, J=5 Hz), 5.62 (1H, dd, J=5 and 8 Hz), 6.70 (1H, s), 7.16 (2H, broads), 9.44 (1H, d, J=8 Hz).

(6) 7-[2-methoxyimino-2-(2-aminothiazol-4-yl)acetamido]-3-[1-[3-(4-ethoxycarbonyl-1-piperazinyl)propyl]-1H-tetrazol-5-yl]thiomethyl-3-cephem-4-carboxylic acid (syn isomer), powder.

I.R. (Nujol): 3300, 1770, 1670, 1600, 1530 cm$^{-1}$.

N.M.R. (DMSO-d$_6$, δ): 1.17 (3H, t, J=6.0 Hz), 2.0 (2H, m), 2.3–2.6 (6H, m), 3.2–3.5 (4H, m), 3.67 (2H, broad s), 3.83 (3H, s), 4.03 (2H, q, J=6 Hz), 4.33 (4H, broad s), 5.13 (1H, d, J=5 Hz), 5.77 (1H, dd, J=5 and 8 Hz), 6.78 (1H, s), 7.15 (2H, broad s), 9.50 (1H, d, J=8 Hz).

(7) 7-[2-(2-cyclopenten-1-yl)oxyimino-2-(2-formamidothiazol-4-yl)acetamido]-3-[1-[3-(4-methyl-1-piperazinyl)propyl]-1H-tetrazol-5-yl]thiomethyl-3-cephem-4-carboxylic acid (syn isomer), powder.

I.R. (Nujol): 3350, 1775, 1670, 1600 , 1550 cm$^{-1}$.

(8) 7-[2-(2-cyclopenten-1-yl)oxyimino-2-(2-aminothiazol-4-yl)acetamido]-3-[1-[3-(4-methyl-1-piperazinyl)propyl]-1H-tetrazol-5-yl]thiomethyl-3-cephem-4-carboxylic acid (syn isomer), powder.

I.R. (Nujol): 3300, 1770, 1660, 1620, 1530 cm$^{-1}$.

EXAMPLE 7

To a solution of N,N-dimethylformamido (277 mg) in tetrahydrofuran (1 ml) was dropwise added a solution of phosphorus oxychloride (583 mg) in tetrahydrofuran (9 ml) at −10° C. and the mixture was stirred at room temperature. After the addition of 2-(2-cyclopenten-1-yl)oxyimino-2-(2-formamidothiazol-4-yl)acetic acid (syn isomer) (900 mg) at −10° C., the resulting mixture was stirred for 30 minutes at 0° C. and then the temperature was raised to 10° C. to give a solution (Solution A). On the other hand, a solution of 7-amino-3-[1-[3-(4-methyl-1-piperazinyl)propyl]-1H-tetrazol-5-yl] thiomethyl-3-cephem-4-carboxylic acid (1.2 g) in a mixture of water (12 ml) and acetone (12 ml) was adjusted to pH 7.0 with a saturated aqueous solution of sodium bicarbonate and then cooled to 0° C. To the solution was dropwise added the above obtained solution A over a period of 5 minutes while the pH was maintained at 7. The resulting solution was allowed to warm to room temperature, stirred for 1.5 hours, adjusted to pH 6.5 with dil, hydrochloric acid and then concentrated under reduced pressure. The precipitates were collected by filtration to give 7-[2-(2-cyclopenten-1-yl)oxyimino-2-(2-formamidothiazol-4-yl)acetamido]-3-[1-[3-(4-methyl-1-piperazinyl)propyl]-1H-tetrazol-5-yl]thiomethyl-3-cephem-4-carboxylic acid (syn isomer) (300 mg). The filtrate was subjected to column chromatography (Non-ion adsorption resin, Diaion HP20 prepared by Mitsubishi Chemical Industries, 60 ml, eluting with water, 5%, 15% and 25% isopropyl alcohol. The fractions containing the object compound were collected and concentrated. The concentrate was lyophilized to give the same object compound (0.85 g), powder.

I.R. (Nujol): 3350, 1775, 1670, 1600, 1550 cm$^{-1}$.

N.M.R. (DMSO-d$_6$, δ): 1.8–3.0 (19H, m), 3.6 (2H, broad s), 4.43 (4H, broad s), 5.07 (1H, d, J=5 Hz), 5.2–5.5 (1H, m), 5.6–62. (3H, m), 7.38 (1H, s), 8.53 (1H, s), 9.55 (1H, d, J=8H).

EXAMPLE 8

The following compounds were prepared according to the simular manner to that of Example 7.

(1) 7-[2-methoxyimino-2-(2-aminothiazol-4yl)acetamido]-3-[1-[3-(4-methyl-1-piperazinyl)propyl]-1H-tetrazol-5-yl]thiomethyl-3-cephem-4-carboxylic acid (syn isomer), powder.

I.R. (Nujol): 3300, 1760, 1660, 1600, 1530 cm$^{-1}$.

(2) 7-[2-methoxyimino-2-(2-aminothiazol-4-yl)acetamido]-3-[1-[3-(4-isopropyl-1-piperazinyl)propyl]-1H-tetrazol-5-yl]thiomethyl-3-cephem-4-carboxylic acid (syn isomer), powder.

I.R. (Nujol): 3300, 1765, 1660, 1600, 1530 cm$^{-1}$.

(3) Sodium 7-[2methoxyimino-2-(2-aminothiazol-4-yl)acetamido[-3-[1-[3-(4-benzyl-1-piperazinyl)propyl]-1H-tetrazol-5-yl]thiomethyl-3-cephem-4-carboxylate (syn isomer), powder.

I.R. (Nujol): 3300, 1760, 1660, 1600 cm$^{-1}$.

(4) Sodium 7-[2-methoxyimino-2-(2-aminothiazol-4yl)acetamino]-3-[1-[3-(4-allyl-1piperazinyl)propyl]-1H-tetrazol-5-yl]thiomethyl-3-cephem-4-carboxylate (syn isomer), powder.

I.R. (Nujol): 3350, 1770, 1670, 1600, 1530 cm$^{-1}$.

(5) Sodium 7-[2-methoxyimino-2-(2-aminothiazol-4-yl)acetamido]-3-[1-[3-(4-phenyl-piperazinyl)propyl]-1H-tetrazol-5-yl]thiomethyl-3-cephem-4-carboxylate (syn isomer), powder.

I.R. (Nujol): 3300, 1765, 1665, 1600, 1530 cm$^{-1}$.

(6) 7-[2-methoxyimino-2-(2-aminothizaol-4-yl)acetamido]-3-[1-[3-[4-(2-hydroxyethyl)-1-piperazinyl]propyl]-1H-tetrazol-5-yl]thiomethyl-3-cephem-4-carboxylic acid (syn isomer), powder.

I.R. (Nujol): 3350, 3250, 1775, 1670, 1610, 1540 cm$^{-1}$.

(7) 7-[2-methoxyimino-2-(2-aminothiazol-4-yl)acetamido] -3-[1-[3-(4-ethoxycarbonyl-1-piperazinyl)propyl]-1H-tetrazol-5-yl]thiomethyl-3-cephem-4-carboxylic acid (syn siomer), powder.

I.R. (Nujol): 3300, 1770, 1670, 1600, 1530 cm$^{-1}$.

(8) 7-[2-methoxyimino-2-(2-aminothiazol-4-yl)acetamido]-3-[1-[2-(4-methyl-1-piperazinyl)ethyl]-1H-tetrazol-5-yl]thiomethyl-3-cephem-4-carboxylic acid (syn isomer), powder.

I.R. (Nujol): 3300, 1765, 1660, 1600, 1530 cm$^{-1}$.

(9) 7-[2-methoxyimino-2-(2-aminothiazol-4-yl)acetamido]-3-[1-(4-methyl-1-piperazinyl)carbonylmethyl-1H-tetrazol-5-yl]thiomethyl-3-cephem-4-carboxylic acid (syn isomer), powder.

I.R. (Nujol): 3300, 1760, 1660, 1600, 1530 cm$^{-1}$.

(10) 7α-methoxy-7β-[D,L-2-carboxy-2-(4-hydroxyphenyl)acetamido]-3-[1-[3-(4-methyl-1-piperazinyl)propyl]-1H-tetrazol-5-yl]thiomethyl-3-cephem-4-carboxylic acid, powder.

I.R. (Nujol): 3200, 1760, 1670, 1600, 1505 cm$^{-1}$.

(11) 7-[2-(2-cyclopenten-1-yl)oxyimino-2-aminothiazol-4-yl)acetamido]-3-[1-3(4-methyl-1-piperazinyl)propyl]-1H-tetrazol-5-yl]thiomethyl-3-cephem-4-carboxylic acid (syn isomer), powder.

I.R. (Nujol): 3300, 1770, 1660, 1620, 1530 cm$^{-1}$.

EXAMPLE 9

A mixture of 7-[2-(2-cyclopenten-1-yl)oxyimino-2-(2-formamidothiazol-4-yl)acetamido]-3-[1-[1-(4-methyl-1-piperazinyl)propyl]-1H-tetrazol-5-yl]thiomethyl-3-cephem-4-carboxylic acid (syn isomer) (1.1 g), methanol (85 ml) and conc.hydrochloric acid (0.6 ml) was stirred for 45 minutes at room temperature. The reaction mixture was adjusted to pH 4.5 with a saturated aqueous solution of sodium bicarbonate and then concentrated. The concentrate was adjusted to pH 7 with a saturated aqueous solution of sodium bicarbonate and then subjected to column chromatography (CM-cephadex, H-type: 110 ml), eluted with 1%, 2%, 4% and 5% aqueous solution of sodium chloride. The fractions containing the object compound were collected and adjusted to pH 4.3 with a saturated aqueous solution of sodium bicarbonate. The resulting solution was subjected to column chromatography (Non-ion adsorption resin, Diaion HP20 prepared by Mitsubishi Chemical Industries: 50 ml), eluting with water and 20% isopropyl alcohol. The fractions containing the object compound were collected and concentrated under reduced pressure. The concentrate was lyophilized to give 7-[2-(2-cyclopenten-1-yl)oxyimino-2-(2-aminothiazol-4-yl)acetamido]-3-[1-(4-methyl-1-piperazinyl)propyl]-1H-tetrazol-5-yl]thiomethyl-3-cephem-4-carboxylic acid (syn isomer) (0.3 g).

I.R. (Nujol): 3300, 1770, 1660, 1620, 1530 cm$^{-1}$.

N.M.R. (DMSO-d$_6$,δ): 1.9–3.2 (16H, m), 2.63 (3H, s), 3.65 (2H, broad s), 4.28 (4H, broad s), 5.06 (1H, d, J=5 Hz), 5.2 (1H, broad s), 5.6–6.3 (3H, m) 6.54 (1H, s), 7.2 broad s), 10.13 (1H, d, J=8 Hz).

EXAMPLE 10

The following compounds were prepared according to the simlar manner to that of Example 9.

(1) 7-[2-methoxyimino-2-(2-aminothiazol-4-yl)acetamido]-3-[1-[3-(4-methyl-1-piperazinyl)propyl]-1H-tetrazol-5-yl]thiomethyl-3-cephem-4-carboxylic acid (syn isomer), powder.

I.R. (Nujol): 3300, 1760, 1660, 1600, 1530 cm$^{-1}$.

(2) 7-[2-methoxyimino-2-(2-aminothiazol-4-yl)acetamido]-3-[1-[3-(4-isopropyl-1-piperazinyl)propyl]-1H-tetrazol-5-yl]thiomethyl-3-cephem-4-carboxylic acid (syn isomer), powder.

I.R. (Nujol): 3300, 1765, 1660, 1600, 1530 cm$^{-1}$.

(3) Sodium 7-[2-methoxyimino-2-(2-aminothiazol-4-yl)acetamido]-3-[1-[3-(4-benzyl-1-piperazinyl)propyl]-1H-tetrazol-5-yl]thiomethyl-3-cephem-4-carboxylate (syn isomer), powder.

I.R. (Nujol): 3300, 1760, 1660, 1600 cm$^{-1}$.

(4) Sodium 7-[2-methoxyimino-2-(2-aminothiazol-4yl)acetamido]-3-[1-[3-(4-allyl-1-piperazinyl)propyl]-1H-tetrazol-5-yl]thiomethyl-3-cephem-4-carboxylate (syn isomer), powder.

I.R. (Nujol): 3350, 1770, 1670, 1600, 1530 cm$^{-1}$.

(5) Sodium 7-[2-methoxyminio-2-(2-aminothiazol-4-yl)acetamido]-3-[1-[3-(4-phenyl-1-piperazinyl)propyl]-1H-tetrazol-5-yl]thiomethyl-3-cephem-4carboxylate (syn isomer), powder.

I.R. (Nujol): 3300, 1765, 1665, 1600, 1530 cm$^{-1}$.

(6) 7-[2-methoxyimino-2-(2-aminothiazol-4-yl)acetamido]-3-[1-[3-[4-(2-hydroxethyl)-1-piperazinyl]propyl]-1H-tetrazol-5-yl]thiomethyl-3-cephem-4-carboxylic acid (syn isomer), powder.

I.R. (Nujol): 3350, 3250, 1775, 1670, 1610, 1540 cm$^{-1}$.

(7) 7-[2-methoxyimino-2-(2-aminothiazol-4-yl)acetamido] -3-[1-[3-(4-ethoxycarbonyl-1-piperazinyl)propyl]-1H-tetrazol-5-yl]thiomethyl-3-cephem-4-carboxylic acid (syn isomer), powder.

I.R. (Nujol): 3300, 1770, 1670, 1600, 1530 cm$^{-1}$.

(8) 7-[2-methoxyimino-2-(2-aminothiazol-4-yl)acetamido]-3-[1-[2-(4-methyl-1-piperazinyl)ethyl]-1H-tetrazol-5-yl]thiomethyl-3-cephem-4-carboxylic acid (syn isomer), powder.

I.R. (Nujol): 3300, 1765, 1660, 1600, 1530 cm$^{-1}$.

(9) 7-[2-methoxyimino-2-(2-aminothiazol-4-yl)acetamido]-3-[1-(4-methyl-1-piperazinyl)carbonylmethyl-1H-tetrazol-5-yl]thiomethyl-3-cephem-4-carboxylic acid (syn isomer), powder.

I.R. (Nujol): 3300, 1760, 1660, 1600, 1530 cm$^{-1}$.

What we claim is:

1. A cephem compound of the formula:

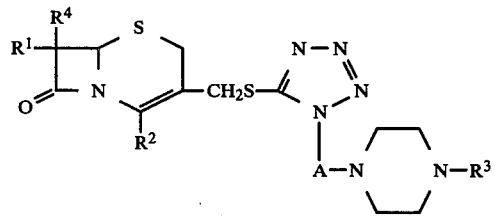

wherein $R^1$ is amino or a protected amino group;

$R^2$ is carboxy or a protected carboxy group;

A is lower alkylene which may have an oxo group;

$R^3$ is carboxy, a protected carboxy group, lower alkyl, lower alkenyl, hydroxy(lower)alkyl, phenyl(lower)alkyl, phenyl, tolyl, xylyl, cumenyl, or naphthyl; and $R^4$ is hydrogen or lower alkoxy, and pharmaceutically acceptable salts thereof.

2. A cephem compound of the formula:

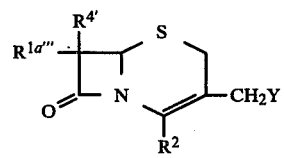

wherein

R$^{1a'''}$ is phenylacetamido having hydroxy and/or carboxy;
R$^2$ is carboxy or a protected carboxy group;
R$^{4'}$ is lower alkoxy; and
Y is a group which can be substituted by a group of the formula:

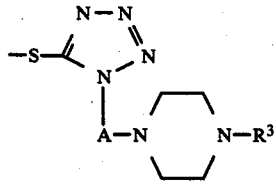

in which A is lower alkylene which may have an oxo group; and
R$^3$ is carboxy, a protected carboxy group, lower alkyl, lower alkenyl, hydroxy(lower)alkyl, phenyl(lower)alkyl, phenyl, tolyl, xylyl, cumenyl or naphthyl.

3. A cephem compound of the formula:

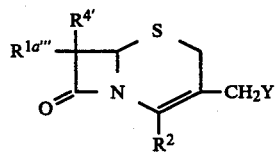

wherein
R$^{1a'''}$ is phenylacetamido having hydroxy or carboxy;
R$^2$ is carboxy or a protected carboxy group;
R$^{4'}$ is lower alkoxy; and
Y is a group which can be substituted by a group of the formula:

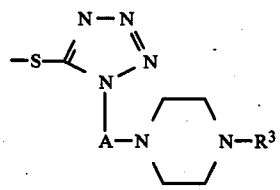

in which A is lower alkylene or lower alkylene having an oxo group; and
R$^3$ is carboxy, a protected carboxy group, lower alkyl, lower alkenyl, hydroxy(lower)alkyl, phenyl(lower)alkyl, phenyl, tolyl, xylyl, cumenyl or naphthyl.

4. A cephem compound of the formula:

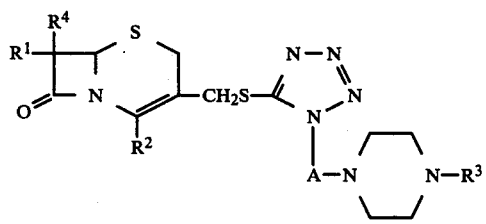

wherein
R$^1$ is 2-lower alkoxyimino-2-(2-aminothiazol-4-yl)-acetamido; 2-cyclo(lower)alkenyloxyimino-2-(2-aminothiazol-4-yl)acetamido; 2-lower alkoxyimino-2-(2-lower alkanoylaminothiazol-4-yl)acetamido; 2-cyclo(lower)alkenyloxyimino-2-(2-lower alkanoylaminothiazol-4-yl)acetamido; or 2-carboxy-2-(4-hydroxyphenyl)acetamido;
R$^2$ is carboxy or a protected carboxy group;
A is lower alkylene or lower alkylene having an oxo group;
R$^3$ is carboxy, lower alkoxycarbonyl, lower alkyl, lower alkenyl, hydroxy(lower)alkyl, phenyl(lower)alkyl or phenyl; and
R$^4$ is hydrogen or lower alkoxy, and pharmaceutically acceptable salts thereof.

5. The compound of claim 2, wherein
R$^1$ is amino; A is lower alkylene; R$^3$ is lower alkyl; and
R$^4$ is hydrogen.

6. The compound of claim 5, which is 7-amino-3-[1-[3-(4-methyl-1-piperazinyl)propyl]-1H-tetrazol-5-yl]thiomethyl-3-cephem-4-carboxylic acid.

7. The compound of claim 2, wherein
R$^1$ is thiazolyl(lower)alkanoylamino, thiazolyl(lower)alkanoylamino having lower alkoxyimino, amino or lower alkanoylamino,
thiazoly(lower)alkanoylamino having cyclo(lower)alkenyloxyimino, amino or lower alkanoylamino or
phenyl(lower)alkanoylamino or phenyl(lower)alkanoylamino having hydroxy or carboxy.

8. The compound of claim 7, which is syn isomer, wherein
R$^1$ is 2-lower alkoxyimino-2-(2-aminothiazol-4-yl)-acetamido;
A is lower alkylene;
R$^3$ is carboxy, lower alkoxycarbonyl, lower alkyl, lower alkenyl, hydroxy(lower)alkyl, phenyl(lower)alkyl or phenyl; and
R$^4$ is hydrogen.

9. The compound of claim 8, which is 7-[2-methoxyimino-2-(2-aminothiazol-4-yl)acetamido]-3-[1-[3-(4-methyl-1-methyl-1-piperazinyl)propyl]-1H-tetrazol-5-yl]thiomethyl-3-cephem-4-carboxylic acid (syn isomer).

10. The compound of claim 8, which is 7-[2-methoxyimino-2-(2-aminothiazol-4-yl)acetamido]-3-[1-[3-(4-isopropyl-1-piperzinyl)propyl]-1H-tetrazol-5-yl]thiomethyl-3-cephem-4-carboxylicacid (syn isomer).

11. The compound of claim 8, which is 7-[2-methoxyimino-2-(2-aminothiazol-4-yl)acetamido]-3-[1-[3-(4-allyl-1-piperazinyl)propyl]-1H-tetrazol-5-yl]thiomethyl-3-cephem-4-carboxylic acid (syn isomer) or its sodium salt.

12. The compound of claim 8, which is 7-[2-methoxyimino-2-(2-aminothiazol-4-yl)acetamido]-3-[1-[3-[4-(2-hydroxyethyl)-1-piperazinyl]propyl]-1H-tetrazol-5-yl]thiomethyl-3-cephem-4- carboxylic acid (syn isomer).

13. The compound of claim 8, which is 7-[2-methoxyimino-2-(2-aminothiazol-4yl)acetamido]-3-[1-[2-(4-methyl-1-piperazinyl)ethyl]-1H-tetrazol-5-yl]thiomethyl-3-cephem-4-carboxylic acid (syn isomer).

14. The compound of claim 7, which is syn isomer, wherein
R$^1$ is 2-lower alkoxyimino-2-(2-aminothiazol-4yl)-acetamido.
A is lower alkylene having an oxo group;
R$^3$ is lower alkyl; and
R$^4$ is hydrogen.

15. The compound of claim 14, which is 7-[2-methoxyimino-2-(2-aminothiazol-4-yl)acetamido]-3-[1-(4-methyl-1-piperazinyl)-carbonylmethyl-1H-tetrazol-5-yl]thiomethyl-3-cephem-4-carboxylic acid (syn isomer).

16. The compound of claim 7, which is syn isomer, wherein
   $R^1$ is 2-cyclo(lower)alkenyloxyimino-2-(2-aminothiazol-4-yl)acetamido;
   A is lower alkylene;
   $R^3$ is lower alkyl; and
   $R^4$ is hydrogen.

17. The compound of claim 16, which is 7-[2-(2-cyclopenten-1yl)oxyimino-2-(2-aminothiazol-4-yl)acetamido]-3-[1-[3-(4-methyl-1-piperazinyl)propyl]-1H-tetrazol-5-yl]-thiomethyl-3-cephem-4-carboxylic acid (syn isomer).

18. The compound of claim 7, wherein
   $R^1$ is 2-carboxy-2-(4-hydroxyphenyl)acetamido;
   A is lower alkylene;
   $R^3$ is lower alkyl; and
   $R^4$ is lower alkoxy.

19. The compound of claim 7, wherein
   $R^1$ is 2-lower alkoxyimino-2-(2-lower alkanoylaminothiazol-4-yl)acetamido or 2-cyclo(lower)alkenyloxyimino-2-(2-lower alkanoylaminothiazol-4-yl)acetamido; and
   $R^4$ is hydrogen.

20. A pharmaceutical antibacterial composition comprising an effective amount of a compound of claim 1 in association with a pharmaceutically acceptable, substantially non-toxic carrier or excipient.

* * * * *

UNITED STATES PATENT AND TRADEMARK OFFICE
CERTIFICATE OF CORRECTION

PATENT NO. : 4,443,443
DATED : April 17, 1984
INVENTOR(S) : Ikuo Ueda et al

It is certified that error appears in the above-identified patent and that said Letters Patent is hereby corrected as shown below:

On the title page change Item [30] to read:

-- [30]  Dec. 17, 1979 [UK]  United Kingdom .......  7943363 --

Signed and Sealed this

Eighteenth Day of September 1984

[SEAL]

Attest:

GERALD J. MOSSINGHOFF

Attesting Officer

Commissioner of Patents and Trademarks